(12) United States Patent
Melosh et al.

(10) Patent No.: US 8,808,516 B2
(45) Date of Patent: Aug. 19, 2014

(54) DEVICES AND METHODS FOR LONG-TERM INTRACELLULAR ACCESS

(75) Inventors: Nicholas Alexander Melosh, Menlo Park, CA (US); Piyush Verma, Mountain View, CA (US); Benjamin David Almquist, Somerville, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 240 days.

(21) Appl. No.: 13/412,543

(22) Filed: Mar. 5, 2012

(65) Prior Publication Data

US 2012/0222970 A1    Sep. 6, 2012

Related U.S. Application Data

(60) Provisional application No. 61/449,615, filed on Mar. 4, 2011.

(51) Int. Cl.
*G01N 33/48* (2006.01)
*G01N 33/18* (2006.01)

(52) U.S. Cl.
CPC ............ *G01N 33/1826* (2013.01); *G01N 33/18* (2013.01)
USPC .... 204/450; 422/68.1; 422/82.01; 435/287.1; 435/29; 73/866.5; 204/280; 204/600; 204/400

(58) Field of Classification Search
CPC ................................................ G01N 33/48728
USPC ................. 204/450, 400, 600; 435/287.1, 29; 422/68.1, 82.01; 205/775; 73/866.5
See application file for complete search history.

(56) References Cited

U.S. PATENT DOCUMENTS

| | | | |
|---|---|---|---|
| 6,368,851 B1 * | 4/2002 | Baumann et al. | 435/285.2 |
| 7,152,616 B2 * | 12/2006 | Zucchelli et al. | 137/68.11 |
| 2004/0182707 A1 * | 9/2004 | Jardemark et al. | 204/451 |
| 2006/0213259 A1 * | 9/2006 | Prinz et al. | 73/104 |
| 2007/0100086 A1 | 5/2007 | Hong et al. | |
| 2011/0168968 A1 | 7/2011 | Yang et al. | |
| 2011/0208031 A1 * | 8/2011 | Wolfe et al. | 600/378 |
| 2012/0276573 A1 | 11/2012 | Vandersarl et al. | |

OTHER PUBLICATIONS

Provisional of 2011/0208031, downloaded Dec. 20, 2013.*
Abhyankar et al.; Characterization of a membrane-based gradient generator for use in cell-signaling studies; Lab Chip; 6(3):389-393; Mar. 2006.

(Continued)

*Primary Examiner* — Jennifer Dieterle
(74) *Attorney, Agent, or Firm* — Shay Glenn LLP

(57) ABSTRACT

Nanoscale probes for forming stable, non-destructive seals with cell membranes. The probes, systems including these probes, and methods of fabricating and using the probes described herein may be used to sense from, stimulate, modify, or otherwise effect individual cells or groups of cells. In particular, described herein are nanoscale cellular probes that may be used to span the lipid membrane of a cell to provide stable and long lasting access to the internal cellular structures. Thus, the probes described herein may be used as part of a system, method or device that would benefit from stable, non-destructive access across a cell membrane. In some variations the nanoscale probe devices or systems described herein may be used as part of a drug screening procedure.

28 Claims, 19 Drawing Sheets

(56) References Cited

OTHER PUBLICATIONS

Ainslie et al.; Microfabricated devices for enhanced bioadhesive drug delivery: attachment to and small-molecule release through a cell monolayer under flow; Small; 5(24):2857-2863; Dec. 2009.
Almquist et al.; Fusion of biomimetic stealth probes into lipid bilayer cores; Proc Natl Acad Sci U S A.; 107(13):5815-5820; Mar. 2010.
Almquist et al.; Nanoscale patterning controls inorganic-membrane interface structure; Nanoscale; 3(2):391-400; Feb. 2011.
Bancroft et al.; Fluid flow increases mineralized matrix deposition in 3D perfusion culture of marrow stromal osteoblasts in a dose-dependent manner; PNAS; 99(20)12600-12605; Oct. 1, 2002.
Boyden; The chemotactic effect of mixtures of antibody and antigen on polymorphonuclear leucocytes; J Exp Med; 115:453-466; Mar. 1, 1962.
Cao et al.; Template-based synthesis of nanorods, nanowire and nanotube array; Adv Colloid Interface Sci; 136(1-2):45-64; Jan. 15, 2008.
Chen et al.; A cell nanoinjector based on carbon nanotubes; Proc Natl Acad Sci U S A.; 104(20):8218-8222; May 15, 2007.
Chu et al.; Electroporation for the efficient transfection of mammalian cells with DNA; Nucleic Acids Res.; 15(3):1311-1326; Feb. 11, 1987.
Dertinger et al.; Generation of Gradients Having Complex Shapes Using Microfluidic Networks; Anal Chem; 73:1240-1246; Feb. 16, 2001.
Diao et al.; A three-channel microfluidic device for generating static linear gradients and its application to the quantitative analysis of bacterial chemotaxis; Lab Chip; 6(3):381-388; Mar. 2006.
El-Ali et al.; Cells on Chips; Nature; 442(7101):403-411; Jul. 27, 2006.
Engler et al.; Matrix Elasticity Directs Stem Cell Lineage Specification; Cell; 126(4):677-689; Aug. 25, 2006.
Gheith et al; Stimulation of Neural Cells by Lateral Currents in Conductive Layer-by-Layer Films of Single-Walled Carbon Nanotubes; Adv Mater; 18(22):2975-2979; Nov. 2006.
Giancotti et al.; Integrin signaling; Science; 285(5430):1028-1032; Aug. 13, 1999.
Goetz et al; Computer simulations of bilayer membranes: Self-assembly and interfacial tension; J Chem Phys; 108(7):7397-7409; May 1, 1998.
Jeon et al.; Generation of Solution and Surface Gradients Using Microfluidic Systems; Langmuir; 16(22):8311-8316; Oct. 31, 2000.
Keenan et al.; Biomolecular gradients in cell culture systems; Lab Chip; 8 (1):34-57; Jan. 2008.
Kim et al.; Interfacing Silicon Nanowires with Mammalian Cells; J Am Chem Soc; 129(23):7228-7229; Jun. 13, 2007.
Kinoshita; Electrochemical Uses of Carbon; Electrochem Encycl; pp. 11; Jan. 2001.
Knez et al.; Synthesis and Surface Engineering of Complex Nanostructures by Atomic Layer Deposition; Adv Mater; 19(21):3425-3437; Nov. 2007.
Langille et al.; Relationship between blood flow direction and endothelial cell orientation at arterial branch sites in rabbits and mice; Circ Res; 48(4):481-488; Apr. 1981.
Loh et al.; Nanofountain-probe-based high-resolution patterning and single-cell injection of functionalized nanodiamonds; Small; 5(14):1667-1674; Jul. 2009.
Lutolf et al.; Synthetic biomaterials as instructive extracellular microenvironments for morphogenesis in tissue engineering; Nat Biotecnol; 23(1):47-55; Jan. 2005.
Patel, et al.; Spatially controlled cell engineering on biodegradable polymer surfaces; FASEB J; 12(14):1447-1454; Nov. 1998.
Persson et al.; Vertical Nanotubes Connected by a Subsurface Nanochannel; 14th Int'l Conference on Miniturized Systems fror Chemistry and Life Sciences; 1862-1864; Oct. 3-7, 2010.
Saito; A Theoretical Study on the Diffusion Current at the Stationary Electrodes of Circular and Narrow Band Types; Rev Polarography; 15(6):177-187; Dec. 1968.
Scadden; The stem-cell niche as an entity of action; Nature; 441 (7097):1075-1079; Jun. 29, 2006.
Shalek et al.; Vertical silicon nanowires as a universal platform for delivering biomolecules into living cells; Proc Natl Acad Sci U S A.; 107(5):1870-1875; Feb. 2, 2010.
Shamloo et al.; Endothelial cell polarization and chemotaxis in a microfluidic device; Lab Chip; 8(8):1292-1299; Aug. 2008.
Tian et al.; Fabrication of high density metallic nanowires and nanotubes for cell culture studies; Microelectronic Eng; 88(8):1702-1706; Aug. 2011.
Uhrich et al.; Polymer systems for controlled drug release; Chem Rev; 99 (11):3181-3198; Nov. 10, 1999.
Verma et al.; Surface-structure-regulated cell-membrane penetration by monolayer-protected nanoparticles; Nat Mater; 7(7):588-595; Jul. 2008 (Author Manuscript; pp. 15).
Verma et al.; Gigaohm resistance membrane seals with stealth probe electrodes; Appl Phys Lett; 97(3):1-3; Jul. 2010.
Walker et al.; Effects of flow and diffusion on chemotaxis studies in a microfabricated gradient generator; Lab Chip; 5(6):611-618; Jun. 2005 (Author Manuscript; pp. 18).
Wang et al.; Neural stimulation with a carbon nanotube microelectrode array; Nano Lett; 6(9):2043-2048; Sep. 2006.
Wang et al.; Shear stress induces endothelial differentiation from a murine embryonic mesenchymal progenitor cell line; Arterioscler Thromb Vasc Biol; 25(9):1817-1823; Sep. 2005.
Whitesides; The origins and the future of microfluidics; Nature; 442 (7101):368-373; Jul. 27, 2006.
Wu et al.; Generation of complex, static solution gradients in microfluidic channels; J Am Chem Soc; 128(13):4194-4195; Apr. 5, 2006.
Xiao et al.; Fabrication of Alumina Nanotubes and Nanowires by Etching Porous Alumina Membranes; Nano Lett; 2(11):1293-1297; Oct. 26, 2002.
Yu et al.; Nano Wheat Fields Prepared by Plasma-Etching Gold Nanowire-Containing Membranes; Nano Lett; 3(6);815-818; Mar. 20, 2003.
Yu et al.; Diffusion dependent cell behavior in microenvironments; Lab Chip; 5 (10):1089-1095; Oct. 2005.
Zicha et al.; A new direct-viewing chemotaxis chamber; J Cell Sci; 99 (4);769-775; Aug. 1991.
Adler et al.; Emerging links between surface nanotechnology and endocytosis: impact on nonviral gene delivery; Nano Today; 5(6):553-569; Dec. 2010 (author manuscript, 15 pgs.).
Bernards et al.; Nanoscale porosity in polymer films: fabrication and therapeutic applications; Soft Matter; 6(8):1621-1631; Jan. 2010 (author manuscript, 13 pgs.).
Black et al.; Upregulation of a silent sodium channel after peripheral, not not central, nerve injury in DRG neurons; J Neurophysiol; 82(5); pp. 2776-2785; Nov. 1999.
Carter; Potent antibody therapeutics by design; Nat Rev Immunol; 6 (5):343-57; May 2006.
Choi; A Cellular Trojan Horse for Delivery of Therapeutic Nanoparticles into Tumors. Nano Letters; 7(12), pp. 3759-3765; Dec. 2007.
Dubey et al.; Intercellular nanotubes mediate bacterial communication; Cell; 144(4):590-600; Feb. 2011.
Gasiorowski et al.; Alterations in gene expression of human vascular endothelial cells associated with nanotopographic cues; Biomaterials; 31(34):8882-8; Dec. 2010 (author manuscript, 15 pgs.).
Geldof; Nerve-growth-factor-dependent neurite outgrowth assay; a research model for chemotherapy-induced neuropathy; J Cancer Res Clin Oncol; 121(11):657-660; Feb. 1995.
Griffith et al.; Polymeric biomaterials; Acta Mater; 48(1):263-277; Jan. 1, 2000.
Hanna et al.; Direct cell reprogramming is a stochastic process amenable to acceleration; Nature;462(7273):595-601; Dec. 2009 (auhor manuscript, 17 pgs.).
Haydon et al.; Anaesthesia by the n-alkanes. A comparative study of nerve impulse blockage and the properties of black lipid bilayer membranes; BBA-Biomembranes; 470(1):17-34; Oct. 3, 1977.
Haydon et al.; The molecular mechanisms of anaesthesia; Nature; 268:356-358; Jul. 28, 1977.

(56) References Cited

OTHER PUBLICATIONS

Heath et al.; Nanotechnology and cancer; Annu Rev Med; 59:251-65; Feb. 2008 (author manuscript, 16 pgs.).

James et al.; Patterned protein layers on solid substrates by thin stamp microcontact printing; Langmuir; 14(4); pp. 741-744; Jan. 1998.

Keenan et al.; Microfluidic fjetsf for generating steady-state gradients of soluble molecules on open surfaces; Appl. Phys. Lett.; 89(11);114103-114103-3; Sep. 11, 2006.

Kubota et al.; Role of laminin and basement membrane in the morphological differentiation of human endothelial cells into capillary-like structures; Journal of Cell Biology; 107; pp. 1589-1598; Oct. 1988.

Kumar et al.; The gap junction communication channel; Cell; 84(3):381-8; Feb. 1996.

Langer; Drug delivery and targeting; Nature; 392(6679 Suppl):5-10.; Apr. 1998.

Lee et al.; Hydrogels for tissue engineering; Chem Rev; 101(7):1869-1879; Jul. 2001.

Luo et al.; Synthetic DNA delivery systems; Nat Biotechnol; 18(1):33-7; Jan. 2000.

Malboubi et al.; Effects of the Surface Morphology of Pipette Tip on Giga-seal Formation. Engineering Letters; 17(4), p. 281; Nov. 2009.

Martin; Nanomaterials: a membrane-based synthetic approach; Science; 266 (5193):1961-6.; Dec. 1994.

McKnight et al.; Tracking gene expression after DNA delivery using spatially indexed nanofiber arrays; Nano Letters; 4(7); pp. 1213-1219; May 2004.

Michalet et al.; Quantum dots for live cells, in vivo imaging, and diagnostics; Science; 307(5709):538-44; Jan. 28, 2005 (author manuscript; 16 pgs.).

Peng et al.; Whole genome expression analysis reveals differential effects of TiO2 nanotubes on vascular cells; Nano Letters; 10(1); pp. 143-148; Jan. 2010.

Petronilli et al.; Transient and long-lasting openings of the mitochondrial permeability transition pore can be monitored directly in intact cells by changes in mitochondrial calcein fluorescence; Biophys J.; 76(2):725-34.; Feb. 1999.

Plath et al.; Progress in understanding reprogramming to the induced pluripotent state; Nat Rev Genet.; 12(4):253-265; Apr. 2011 (author manuscript, 26 pgs.).

Qi; Cell adhesion and spreading behavior on vertically aligned silicon nanowire arrays; ACS Appl Mater Interfaces; 1(1):30-4; Jan. 2009.

Ruoslahti; New perspectives in cell adhesion: RGD and integrins; Science; 238(4826):491-7; Oct. 1987.

Safran et al.; Database update: GeneCards version 3: the human gene integrator; Database (Oxford); vol. 2010 (baq020); 16 pgs.; Aug. 2010.

Sakiyama-Elbert et al.; Controlled release of nerve growth factor from a heparin-containing fibrin-based cell ingrowth matrix; J Control Release; 69(1):149-158; Oct. 3, 2000.

Susin et al.; Molecular characterization of mitochondrial apoptosis-inducing factor; Nature; 397; pp. 441-446; Feb. 1999.

Tian et al.; Three-dimensional, flexible nanoscale field-effect transistors as localized bioprobes; Science;329(5993):830-4; Aug. 2010 (author manuscript, 11 pgs.).

Tiscornia et al.; A general method for gene knockdown in mice by using lentiviral vectors expressing small interfering RNA; Proc Natl Acad Sci U S A.; 100(4):1844-1848; Feb. 18, 2003.

Xie et al.; Vertical nanopillars for highly localized fluorescence imaging; Proc Natl Acad Sci U S A.; 108(10):3894-9; Mar. 2011.

Yang et al.; Semiconductor nanowire: What's Next?; Nano Letters; 10; pp. 1529-1536; May 2010.

Zeck et al.; Noninvasive neuroelectronic interfacing with synaptically connected snail neurons immobilized on a semiconductor chip; Proc Natl Acad Sci U S A.; 98(18):10457-62; Aug. 2001.

Zigmond; Orientation chamber in chemotaxis; Methods Enzymol; 162:65-72; Oct. 12, 1988.

\* cited by examiner

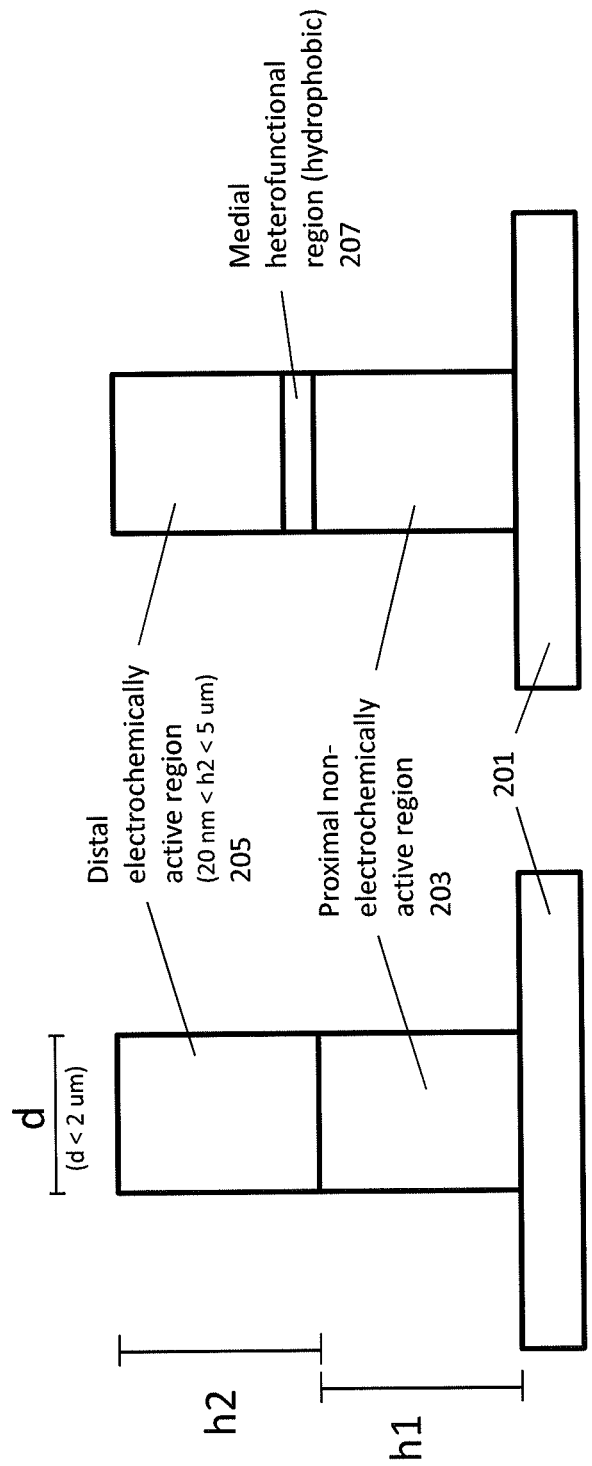

| $l_p$/nm | $l_b$ (%) | $\Delta G_{def}$ per nm/$k_bT$ nm$^{-1}$ | $\Delta G_{phobic}$ per nm/$k_bT$ nm$^{-1}$ |
|---|---|---|---|
| 2 | 64.5 | 4.3 | 6.7 |
| 5 | 161.3 | 13.1 | 11.6 |
| 10 | 322.6 | 173.0 | 42.0 |

DEVICES AND METHODS FOR LONG-TERM INTRACELLULAR ACCESS

CROSS REFERENCE TO RELATED APPLICATIONS

This patent application claims priority to U.S. Provisional Patent Application No. 61/449,615, titled "DEVICES AND METHODS FOR LONG-TERM INTRACELLULAR ACCESS" and filed on Mar. 4, 2011.

STATEMENT OF GOVERNMENT SUPPORT

This invention was made with government support under 0425897 awarded by the National Science Foundation. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are nano-scale devices, systems and methods for accessing a cell or cells without compromising the cell lipid bilayer or the cell's chemical composition and health. Such devices, systems and methods may provide useful for various applications including, but not limited to, drug discovery, drug delivery, gene delivery, biomedical imaging, intracellular implants and pacemakers.

BACKGROUND

Stably and nondestructively positioning artificial materials across living cell membranes is a long-held goal of biomaterials. Accessing the intracellular space of a cell is of essential importance in many different biomedical applications. The ability to specifically and nondestructively incorporate inorganic structures into or through biological membranes is a key step toward realizing full bioinorganic integration in applications such as drug delivery, electrical recording and stimulation, targeted cellular therapeutics, and biosensors. Interfaces for the delivery of inorganic objects across cell membranes generally rely upon destructive formation of membrane holes and serendipitous adhesion, rather than selective penetration and attachment into the bilayer itself. A more benign means to penetrate through the cell membrane is required. While surface modification techniques have been highly successful at controlling cell mobility, proliferation, and differentiation on two-dimensional surfaces, bridging across the cell membrane itself has been much less studied.

In nature, membrane proteins are examples of systems whose outer surface is designed to specifically interact with the interior of the cell membrane lipid bilayer. The tight junction between the lipid and protein eliminates constitutive ion or protein leakage, allowing membrane proteins to regulate the chemical flux through the bilayer. This relationship has been difficult to achieve with man-made biomaterials. Although many man-made biomaterials are designed to regulate the interactions between artificial and natural surfaces, including across the cell membrane, when such materials are inserted through the cell membrane the interface formed between the interior edge of the membrane and the material surface is not well understood and poorly controlled.

While many gene and drug carrier particles appear to enter the cell by endocytotic mechanisms, materials such as cationic polymers and nanoparticles have been shown to directly penetrate the membrane. However, these highly charged species can create holes leading to significant cytotoxicity, and the underlying lipid-cation interaction mechanism is still poorly understood. New materials delivery systems such as DNA functionalized nanowires pierce the membrane and have had some success delivering cargo, but cells are unable to survive longer than several days following penetration.

Thus, nanomaterials and nanostructured surfaces offer new opportunities to interact with biological species at their native length scales, promising more effective interfaces if the appropriate architectures can be discovered. In particular, engineered interfaces between nanostructures and lipid bilayers, themselves nanoscale two-dimensional fluids approximately 5 nm thick, may provide a unique means to breach this defensive wall enabling direct chemical and electrical access to the cell's interior. Technologies for drug delivery, electrical (e.g., ion-channel) measurements, single cell analysis, and gene therapy would all benefit from an improved understanding of how to establish direct chemical and electrical conduits to the cell's interior without inducing detrimental side effects. While there are existing methods for gaining intracellular access, the techniques tend to be destructive (electroporation and patch-clamping), slow (microinjection and patch-clamping), or inefficient (liposomal delivery and endocytotic uptake).

For example, direct electrical access into the cell interior is required for low-noise recording of ion channel activity; yet conventional patch clamp techniques are destructive, leading to rapid cell death, while on-chip devices have poor seal resistances. Yet there is a huge potential benefit if electrodes that nondestructively incorporate into biological membranes could be realized. For example, the patch-clamp technique has been the gold standard for fundamental studies relating to the electrical properties of cells. These experiments have included whole cell behavior down to individual ion channel activity, and have become a critical tool for the discovery of drugs that affect these proteins. The conventional "whole-cell" patch-clamp involves gently pressing a fine glass micropipette 1-2 µm in diameter against the cell membrane and applying suction, tearing a hole in the membrane for intracellular access, and forming a high-resistance seal with the membrane. While the actual structure of the membrane-pipette interface is not understood, the patch-clamp technique is highly successful at forming tight seals with resistances of several gigaohms. This gigaohm seal enables the measurement of ion channel currents with extremely high signal-to noise ratio. However, the rapid apoptosis of patched cells (approximately 2 h), small number of simultaneous measurements (e.g., 2-3), and inherently serial process have limited applicability of conventional patch-clamping for monitoring cell behavior over extended periods. To overcome these limitations, planar chip-based and automated patch clamp devices have been developed. These existing chip-based electrodes are based on arrays of micromachined holes formed in the substrate or suspended insulating layer as on-chip facsimiles of the pipette tip. Although successful at accelerating the patch clamping process, these devices suffer from low gigaohm seal formation rates and the same rapid cell apoptosis as traditional patch-clamp methods. Efforts to improve seal resistance have largely focused on homogeneously modifying the inorganic materials, including silicon oxide coated nitride membranes, silicon coated with plasma-enhanced chemical-vapor deposited oxide, silicon elastomers, polydimethylsiloxane, glass and quartz and varying the surface roughness, all with limited success. Ideally, chip-based solid state electrodes could enter the cell without causing cell apoptosis, yet previous attempts could not achieve the high-resistance membrane seals necessary.

The lipid bilayer itself is composed of two lipid leaflets, and consists of three different zones: external hydrophilic head groups, hydrophobic lipid tail groups that form the lipid core, and internal hydrophilic head groups. In their liquid state, lipids in the bilayer are highly mobile species, with the structure a dynamic balance between the hydrophobicity of the tail groups, stretching/compression of the tails, head group repulsion, and the relative head to tail dimensions. Because of this mobility, a wide array of lipid bilayer structures has been observed, including vesicles, lamellar sheets, triple junctions, tubules, and platelets. Small molecules and even some nanoparticles have been shown to be able to partition into and through the bilayer without dramatically altering its organization. However, when larger materials penetrate the bilayer an edge or interface must be created. The structure of this new interface is not clear, yet would be anticipated to depend upon the material's nanoscale morphology and hydrophobicity.

FIG. 1 shows four scenarios for bilayer interface structure after material penetration. The first (FIG. 1A) is an idealized 'fused' state, where the bilayer makes intimate contact with the probe with little or no disruption of the lipid organization. This is most reminiscent of transmembrane protein interfaces, which often have the first layer of lipids transiently adsorbed on the protein surface. The uninterrupted hydrophobic layer and tight interface serve as a significant barrier for ion or fluid flow, preventing exchange from one side of the membrane to the other. Indeed, cell membranes can have electrical resistances ranging from 10-100 Gigaohms (GΩ) implying almost no ion leakage occurs at the thousands of protein-membrane interfaces. This scenario likely requires nanoscale modification of the probe surface, since it simultaneously interacts with both the hydrophilic and hydrophobic zones of the lipid bilayer.

The second structure (FIG. 1B) is the 'T-junction' configuration. This architecture essentially splits the bilayer into two monolayers in which each contact the probe surface, similar to triple-bilayer junctions observed in the hemifusion state during membrane fusion. This arrangement may be energetically favorable for hydrophobic probes, since the surface is in contact with the hydrophobic bilayer tails. A key aspect to this arrangement is the formation of an unfavorable empty interstice, or void, where the bilayer splits, estimated to cost about $10\ k_bT$ per nm length of interstice. In hemifused junctions between flexible lipid vesicles this energy can be reduced by increasing the local curvature and lipid splay, however in this case the bilayer must conform to the stiff probe surface and is thus largely unable to do so. This state may therefore be weaker than the fused state. Related structures, such as membrane stalks, have been predicted to increase the rate of hole formation in the surrounding membrane, which could also destabilize this interface. The third situation (FIG. 1C) is the 'ruptured' state where the bilayer forms a hole around the probe with a hydrophilic lipid edge near the probe surface but not in direct contact. This may be the favored configuration for hydrophilic probe surfaces since both materials are in continuous contact with water, however, the gap allows fluid and ions to diffuse through the interface. The leakage rate through the junction could vary greatly depending upon the separation between the edge and the probe surface and may fluctuate over time. Energy considerations and molecular dynamics simulations imply that the ruptured bilayer edge consists of a hemispherical cap of lipids which shield the hydrophobic core from the aqueous phase. The curvature and partial exposure of the tail groups make the edge a relatively high energy state, with line energies on the order of $10\ pJ\ m^{-1}$. This is still considerably smaller than direct lipid tail-water contact, which can be estimated using typical alkane-water surface energies of $25\ mJ\ m^{-2}$ to be roughly $75\ pJ\ m^{-1}$ for a 3 nm thick bilayer core. While at equilibrium holes in the membrane are unusual, they are commonly created by artificial means such as electroporation or mechanical tension, thus are not unlikely for penetrating probes.

The final scenario (FIG. 1D) is the 'adhered' state, in which the lipid surface is attached to the surface of the probe. Lipid-surface adhesion is common in supported lipid bilayers, driven by electrostatic and van der Waals attractions. The lipid is usually not in direct contact with the surface, instead separated by a 1-2 nm aqueous gap. This gap allows some ion transport through the junction as measurements have found conductivities of approximately $0.002\ \Omega^{-1}\ cm^{-1}$ for model lipid/glass interfaces, yet larger proteins may be prevented from passing. This is thought to be the interface created during patch-clamp measurements, and with sufficient surface contact area could be highly resistive.

The specific nature of the probe/lipid junction is important for the mechanical strength, electrical resistivity, and cytotoxicity of the interface. For non-destructive interfaces to cells and membranes, the fused state is likely optimal by preventing leakage from the cytosol and maintaining strong attachment. However, to date, a fused seal such as shown in FIG. 1A has not been possible to reliably achieve. Described herein are devices, systems, and methods for forming stable, long-lasting and non-destructive fused seals with cells. The devices, systems and methods described herein may address the goals and limitations of other technologies discussed above.

SUMMARY

The present invention relates to probes for forming stable, non-destructive seals with cell membranes. The devices, systems and methods described and illustrated may be used to form probes (including probe electrodes) that can be used to sense, stimulate, measure, or otherwise modulate cells. These devices, systems and methods may be used as part of any other system, methods or device that would benefit from stable, non-destructive access across a cell membrane. For example, the devices described herein may include probes or arrays of probes for recording cellular membrane potentials in response to an applied or observed stimulus. Similarly, the devices described herein may be used to form part of a biological interface for a medical device (such as an implant, prosthetic, or the like). These probes could also be used to deliver material across the membrane, or to transport functional materials or devices into the cell. In one example, this could be antibodies meant to capture specific molecules within the cell, or genetic material such as DNA or RNA. In some variations the devices or systems described herein may be used as part of a drug screening procedure. These devices could also form part of a drug delivery system, either for cells in vitro, or tissues in vivo such as a transdermal patch.

For example, described herein are probes that may be used to stably fuse into or through a cell. These probes may be probe electrodes for electrical recording from near or within the cell. In some variations the probe electrodes include: a base region including an electrical contact; and a post projecting from the base region, the post having a diameter of less than about 2 um, the post comprising: a distal electrochemically active region in electrical communication with the electrical contact; and a proximal non-electrochemically active region adjacent to the base region. Here, electrochemically active refers to both electron transfer processes ('Faradaic' reactions), and capacitive or other non-Faradaic processes.

In general, the base region has an outer surface (e.g., coating, layer, region) of a hydrophilic material that is electrically insulative, except for the electrical contact. The post (which may be cylindrical, conical, tubular, or any other appropriate shape) extends from the base. The post has at least two regions (e.g., a distal electrochemically active region and a proximal non-electrochemically active region). In general this post may be hydrophilic, except that in some variations a medial heterofunctional region separates the distal electrochemically active region from the proximal non-electrochemically active region. The post may stand proud (e.g., perpendicular or substantially perpendicular) from the base. In some variations, the post extends at an angle (e.g., 30°, 45°, 50°, 60°, etc.) with respect to the base.

The overall geometry of the post may be configured to allow it to engage a cell. For example, the probe may include a post having an outer diameter, d, of less than 1000 nm (e.g., less than 400 nm, less than 300 nm, less than 200 nm, etc.). The height may be generally less than 50 µm (e.g., less than 40 µm, less than 20 µm, less than 15 µm), and is greater than 200 nm (e.g., greater than 300 nm, greater than 0.5 µm, greater than 1 µm, greater than 5 µm, etc.).

In general, the distal electrochemically active region is able to pass current with applied voltage either through faradic or capacitive mechanisms. For example, this region may be formed of a material so that it can perform both capacitive (e.g., non-faradic) coupling to a solution such as the cytoplasm, or pass faradic current. Thus, the region may pass current (positive or negative) between the solution and the electrode. The distal electrochemically active region is typically in electrical contact with the conductive electrical contact region in the base.

In some variations the distal electrochemical region has a height of between about 20 nm and about 5 µm. The distal electrochemical region may be nanoporous, or may be formed of a material having nanopores. For example, the distal electrochemical region may be formed of one or more materials such as: Pt; PtO; Ir; IrO; $Ir_2O_3$; $IrO_2$; Ru; $RuO_2$; diamond; Au; graphite; Ni; V; Co; W; Mn; oxides of: Pt, PtO, Ir, IrO, $Ir_2O_3$, $IrO_2$, Ru, $RuO_2$, diamond, Au, graphite, Ni, V, Co, W, Mn; polyanaline; and poly(3,4 ethylene dioxythiophene). Additional electrode materials include V, W, Ce and their respective oxides. Organic materials with good electrochemical properties can also be used, such as polyanaline, poly(3,4 ethylene dioxythiophene) (PEDOT), or carbon black. In general, these materials are nontoxic within a cell, and the entire electrochemical region may be generally hydrophilic.

The proximal non-electrochemically active region typically connects to the base, and in some variations is formed of the same material (e.g., an electrical insulator such as $SiO_2$, $Al_2O_3$, polymer, etc.), or is integrally formed with the base. A conductor or conductors may be positioned within the proximal non-electrochemically active region. Thus, in some variations the proximal non-electrochemically active region is formed by an outer coating or layer that is an insulator. For example, in some variations the probe electrode includes a conducive region in electrical contact with the distal electrochemically active region that extends through the proximal non-electrochemically active region to a connector on the base.

As mentioned above, in some variations the probe electrode includes a medial heterofunctional region in an annular ring between the distal electrochemically active region and the proximal non-electrochemically active region, wherein the medial heterofunctional region is configured to form a region that is more hydrophobic than either the distal electrochemically active region or the proximal non-electrochemically active region. In some variations this medial heterofunctional region is referred to as an annular hydrophobic region.

In general, the medial heterofunctional region is configured to enhance insertion of the post into the cell membrane. The medial heterofunctional region is configured to be a region of hydrophobicity that is distinct from the upper (distal) and lower (proximal) surfaces. As described in detail below, this region may be "heterofunctionalized" to form a hydrophobic region that can readily insert into the membrane. Alternatively, or in addition, a functionalized region may be included that can bind and deliver bioactive molecules (peptides, DNA, viruses or dyes) for delivery and/or release. The medial heterofunctional region may be dimensioned and configured for this purpose; for example, the medial heterofunctionalized region may be an annular region separating the distal electrochemically active and the proximal non-electrochemically active regions. For example, the medial heterofunctional region may have a width of less than 200 nm (e.g., less than 100 nm, less than 25 nm, etc.). This region may form a hydrophobic band that is surrounded on either side (e.g., distally and proximally) by hydrophilic regions. In some variations the medial heterofunctional region has a width of between about 5 nm and about 10 nm, similar to the dimensions of the lipid membrane. The properties of this hydrophobic band generally reflect those of transmembrane protein domains, and are often hydrophobic. The width in this context may refer to the width along the proximal-to-distal length of the post forming the probe, which may also be referred to as the height of this region. In general the widths of any of the regions described herein may be the same along the perimeter of the post; however, in some variations the width may vary along the perimeter.

In some variations the medial heterofunctional region is formed of a material that allows self-assembly of one or more materials that will compose the hydrophobic band of the medial heterofunctional region; in other variations the medial heterofunctional region is formed by a coating or direct attachment of material forming the hydrophobic band. For example, in some variations the medial heterofunctional region is formed of a metal (e.g. nickel) to which hydrophobic molecules (such as proteins and/or other organic molecules) bind. In some variations the outer material is formed of a polymer providing a hydrophobic outer region. Examples include using a Au, Ag or Cu layer, onto which molecules with a thiol or sulfide group may bind. Other examples of self-assembly pairs of molecules and their respective substrates are isocyanates on Pt, carboxylic acids on titanium oxide, alkoxy silanes on silicon oxide. Examples of molecules attached include alkane thiols, alkane thiol derivatives, peptide sequences, and short polymers. In one implementation, this may be assembly of butane thiol molecules on a Au heterofunctional band.

The medial heterofunctional region may be formed of sequential layers of hydrophobic and hydrophilic bands (e.g., repeated medial heterofunctional regions separated by hydrophobic bands). This configuration may help allow cells to fuse to one or more bands of the medial heterofunctional region somewhat independently of the height/position of the medial heterofunctional region relative to the post. This may also allow use of the probes with cells of different dimension and configurations.

In some variations, the devices and systems described herein include additional regions (in addition to the distal electrochemically active region, the proximal non-electrochemically active region and the medial heterofunctional region). These regions may provide additional (or alternative) functionality to the post. For example, in some variations the post includes one or more secondary medial regions located distal to a medial heterofunctional region. The secondary medial region is also configured to form a hydrophobic region. Such regions may engage cellular (e.g., intracellular) structures or domains, such as the nucleus or endoplasmic reticulum.

Additional regions may include other probes or markers that may indicate status or activity of a cell bound to the post. For example, in some variations a probe electrode includes a functionalized region distal to the proximal non-electrochemically active region, wherein the distal functionalized region comprises an activity marker configured to indicate a cellular state or activity. Examples of such markers include, but are not limited to, florescent markers, specific binding markers (such as antibodies, calcium binding agents, etc.), genetic material (DNA, RNA) or functional materials such as nanoparticles or drug delivery vehicles. A distal functionalized region may include one or more functional markers (such as calcium markers, enzymatic markers, etc.), which may be visualized. For example, such markers may be fluorescent. In some variations binding of a target molecule may change the florescence signal (e.g., FRET, etc.).

In some variations a distal functionalized region includes a manipulative function within the cell. For example, the region may include an siRNA, chelator, etc. This region may therefore include a compound or molecule that is desired for delivery within the cell; such compounds may be bound to a region of the post, or they may be releasable (e.g., once the post is within a cell).

Also described herein are probes (e.g., probe electrodes) for inserting though a cell membrane, the probe electrode comprising: a base region; a post projecting from the base region, the post having a diameter of less than about 2 µm, the post comprising: a distal electrochemically active region; a proximal non-electrochemically active region adjacent to the base region comprising an electrically insulating material; and a medial heterofunctional region between the distal electrochemically active region and the proximal non-electrochemically active region, wherein the medial heterofunctional region is configured to form a region that is more hydrophobic than either the distal electrochemically active region or the proximal non-electrochemically active region so that a cell membrane may fuse to the medial heterofunctional region.

As mentioned above, the medial heterofunctional region may comprise an annular ring configured to bind to a molecule to form an annular hydrophobic region separating the distal electrochemically active region and the proximal non-electrochemically active region.

In some variations, described herein are probe electrodes for inserting through a cell membrane, the probe electrode comprising: a base region including an electrical contact; and a post projecting distally from the base region, the post having a diameter of less than about 2 µm, the post comprising: a distal electrochemically active region in electrical communication with the electrical contact; a proximal non-electrochemically active region that is electrically insulating and adjacent to the base region; a medial heterofunctional region between the distal electrochemically active region and the proximal non-electrochemically active region, the medial heterofunctional region configured to form an annular hydrophobic region between the distal electrochemically active region and the proximal non-electrochemically active region.

Methods of using probes are also described and illustrated herein. These methods may be used to record (e.g., electrically record) from a cell or cells. For example, described herein are methods of electrically recording from a cell, the method comprising: contacting a cell membrane with a probe electrode comprising a base region and a post projecting from the base region, the post having a diameter of less than about 2 µm, a distal electrochemically active region, and a proximal non-electrochemically active region; and forming a seal with the cell membrane so that the electrochemically active region is in electrical communication with the cell.

Also described herein are methods of establishing stable intracellular transmembrane access with a cell, the method comprising: contacting the cell with a probe electrode having a base region and a post projecting from the base region, the post having a distal electrochemically active region and a proximal non-electrochemically active region, wherein the distal electrochemically active region is separated from the proximal non-electrochemically active region by a medial heterofunctional region forming a hydrophobic band around the post; and fusing the hydrophobic band into the cell membrane.

The layout of the probes may be designed to encourage more than one probe to be integrated into a single cell. For example, in some variations two or more probes may be spaced more closely than the average cell diameter such that both posts may contact, be near, and/or enter the same cell. For example, in some variations pairs or groups (e.g., groups of 2, 3, 4, 5, or more) of posts are spaced less than 50 µm apart, less than 25 µm apart, less than 20 µm apart, less than 15 µm apart, less than 10 µm apart, less than 5 µm apart, etc. This may provide additional benefit by allowing one post to perform current injection functions, while the other may record the voltage. This probe arrangement may provide an accurate way to reduce electrical recording artifacts and allow contact resistance to be removed from the signals. Alternatively, these probes could be used to record from different areas in the cell, reducing the amount of space-charge resistance caused by the resistivity of the surrounding fluid. More than two probes per cell can also be designed by producing many probes spaced less than the average cell diameter. For example, three or more probes could be used to triangulate the location of an electrical event within the cell. In some variations, probes are arranged in clusters or groups, and the groups are separated by more than a typical single cell diameter.

Although in many of the variations described herein the probes are configured for electrically recording from one or more cells, in some variations the probes may be adapted for recording from cells without electrically recording. In some configurations it may be desirable to use the nanostructured probes described to form a stable seal with a cell membrane without electrically recording from within the cells. For example, in some variations the distal end of the probe may not include a distal electrochemically active region but may include a functionalized region distal to the medial heterofunctional region. Thus, the probe may have a generally hydrophilic structure with a medial ring or of hydrophobic material allowing fusion and/or seal to a cell (a medial heterofunctional region); a region distal to the medial heterofunctional region may be functionalized to include or attach one or more molecular probes (e.g., functional markers such as calcium markers, enzymatic markers, antibodies, siRNA, nanoparticles, etc.) which may include one or more indicators or sensors (e.g., florescent labels, etc.) that can be stably introduced into the cell by the post. In such variations it may not be necessary or desirable to include the distal electrochemically active region. Such post variations may provide sensors for monitoring cellular activity and/or behavior based on the functionalized region.

Similarly, in some variations a second medial region may be included. As mentioned above, a secondary medial region can be used to orient a cellular sub-region (e.g., nucleus, etc.) with respect to the probe, potentially allowing intracellular targeting or sensing. In some variations the cells may respond to the probe structures by growing, orienting or otherwise adapting in a manner.

BRIEF DESCRIPTION OF THE DRAWINGS

FIG. 2A is a schematic of one variation of a heterometallic probe electrode. FIG. 2B shows another variation of a probe electrode.

FIG. 4A shows Ni bottom electrodes patterned on an insulating substrate, and a 300/10/100/20 nm Ti/Au/Ti/Pt post is deposited on top. FIG. 4B shows a 10 nm alumina passivation layer deposited with atomic layer deposition. In FIG. 4C, FIB milling etches the side walls to expose the gold band. In FIG. 4D, PMMA is deposited for passivation and the gold band functionalized with butanethiol. FIG. 4E shows an SEM micrograph of the post before FIB milling. FIG. 4F shows SEM micrograph of the post after milling, showing the exposed Au layer. In FIG. 4G, Auger electron spectroscopy elemental composition map clearly shows the Pt top, Au edge, and Ti layers.

FIG. 5A shows a large reduction in current is observed for butanethiol functionalized probes, corresponding to formation of a gigaohm seal with a resistance of $3.8\pm1.9$ G$\Omega$. In FIG. 5B, for the unfunctionalized control probe (without a hydrophobic medial heterofunctionalized region/band), only a small reduction in current is observed as the cell contacts the post.

FIG. 7A shows surface-surface interactions regulated by tethering molecules to the substrate. FIG. 7B shows one variation of a probe structure with a hydrophobic domain designed to interact specifically with the hydrophobic membrane core through selective surface functionalization. FIG. 7C shows a functionalized band several nanometers thick defined by selective self-assembly of molecules. In FIG. 7D, a hydrophobic functionalized band interacts specifically with the hydrophobic core of the lipid bilayer, similar to the behavior of membrane proteins.

In FIG. 8A, a Si AFM tip is used to fabricate probes as described herein. FIG. 8B shows that, using the focused ion beam microscope (FIB), the tip was shaped into a post of approximately 500 nm in diameter. In FIG. 8C, the Cr—Au—Cr metal films were evaporated onto the entire cantilever and post, covering the top and sidewalls of the milled post. FIG. 8D illustrates tips that were remilled in the FIB to trim the excess metal from the sidewalls of the post and expose the edge of the Au layer. Final tip diameter in this example is approximately 200 nm. FIG. 8E illustrates fabricated tips that were subsequently functionalized using alkanethiol self-assembly. FIGS. 8F-8H shows SEM images of corresponding fabrication steps (FIGS. 8A-8C). FIG. 8I shows a TEM image of a final version of a probe electrode. FIG. 8J shows the TEM image of layered metal stack at tip of stealth probe. The 10 nm Au band (dark, central band) is visible between the two Cr layers, with a clean edge profile.

FIG. 10A shows an unfunctionalized probe. FIG. 10B shows a 10 nm Au/butanethiol functionalized probe. FIG. 10C shows a 10 nm Au/dodecanethiol functionalized probe. (Insets show timescale of interface rupture for the tear-off event).

FIG. 13A shows standard Si AFM cantilevers are used as a basis for fabrication. In FIG. 13B FIB milling is used to create an approximately 500 nm post. FIG. 13C metal deposition (e-beam, sputtering) is used to deposit a layered Cr—Au—Cr structure. FIG. 13D shows evaporated tips are re-milled in the FIB to a final diameter of approximately 200 nm. In FIG. 13E, Au bands are rendered hydrophobic via thiol-mediated self-assembly. FIG. 13F shows a TEM image of a 10 nm Au band (dark, central band) at the end of a milled post. FIG. 13G shows probe geometries used in this study.

In FIG. 14A stealth probes pressed against a stack of lipid bilayers, causing the tip to jump from bilayer core to bilayer core as it penetrates the stack. FIG. 14B shows testing results in characteristic stair-step curves as a function of time. In FIG. 14C, the breakthrough rate as a function of force is plotted in order to extract the unstressed energy barriers for each probe.

In FIG. 19A, (l=(2/5)d) the bilayer fused with band, homogenous and ordered interface. In FIG. 19B, (l=(3/5)d) the bilayer forms 'fused' interface with band. In FIG. 19C, (l=d) the bilayer fused with band, no void formation. In FIG. 19D, (l=(6/5)d) the bilayer fuses to the band, small interstice void formed. FIG. 19E, (l=(8/5)d) shows disordered fusion, large interstice void formed with a bilayer pore (see also FIG. 20). FIG. 19F illustrates homogenous functionalization resembling N-probes. Bilayer fuses to surface in a 'T junction' by splitting into two monolayers. Small interstices present, yet pores are common.

FIG. 20A shows a top view for l=(2/5)d, which shows uniformity of interface along band length. FIG. 20B shows a top view for l=(8/5)d, and shows a bilayer pore indicating leaky and weak interface. In FIG. 20C, showing a front view for l=(2/5)d bilayer fused with band, homogenous and ordered interface. In FIG. 20D, a front view for l=(8/5)d shows incomplete fusion, heterogeneous disordered interface. FIG. 20E is a 3-D view of equilibrium interface structure for l=(2/5)d. FIG. 20F is a 3-D view of equilibrium interface structure for l=(8/5)d.

DETAILED DESCRIPTION

Figures 1A, 1B, 1C, 1D:
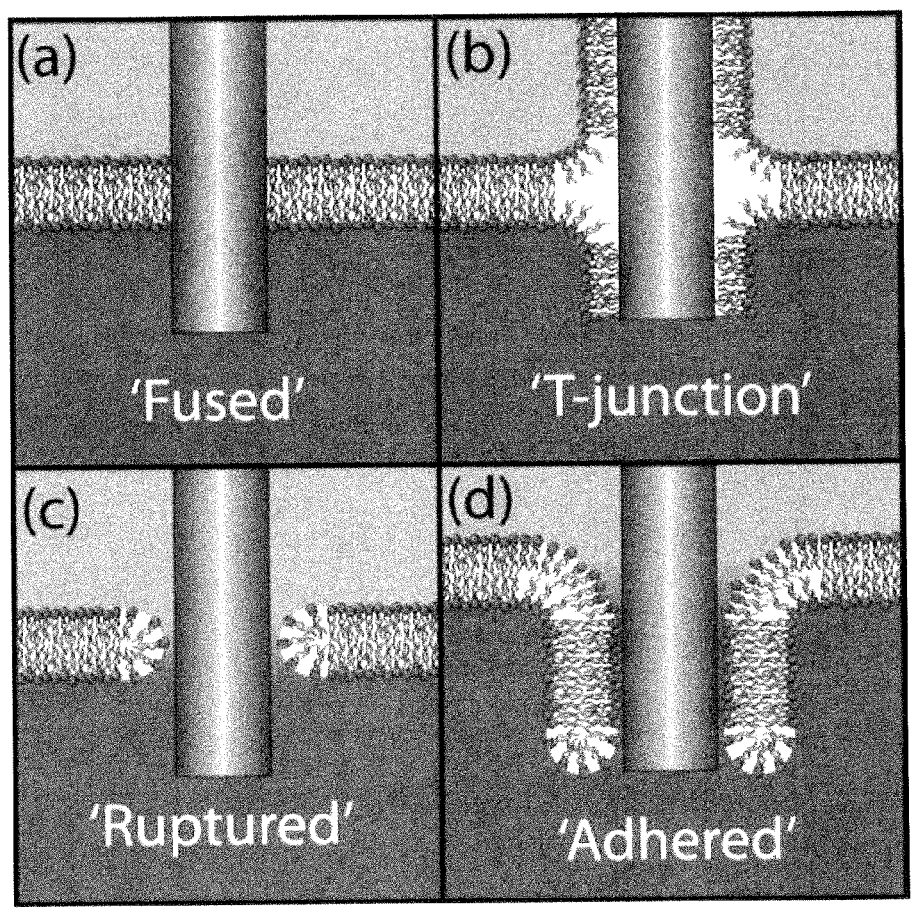
FIGS. 1A-1D show different scenarios of lipid interfaces to penetrating probe materials.

In general, described herein are nanoscale probes projecting from a base for fusing with a cell membrane to provide access across the cell membrane. These probes may be used to record or measure cellular behavior or activity, and/or to apply one or more materials to the cell and/or to stimulate or modify cellular activity. For example, probe electrodes are described herein. For convenience, the nanoscale probes described herein may also be referred to as "stealth" probes.

In many of the variations described herein the probes may be configured by controlling the dimensions and materials of the probe to form a tight seal with a cell membrane. In some variations the probes are generally hydrophilic but include one or more transverse hydrophobic regions that are configured to insert into the lipid bilayer of a cell. The dimensions and position of the hydrophobic region may be chosen to permit fusion and maintenance of the seal stably over a long time period. In some variations the probe may include different functionalized regions that controllably interact with the cell and/or cell membrane.

FIG. 2A illustrates a first generalized version of one variation of a nanoscale probe for sealing with a cell membrane. In FIG. 2A the cell is shown as a schematic side view of a heterometallic probe. In this example the probe includes a base or base region 201 from which a proximal 203 and distal 205 projecting region extends. The proximal 203 region is a proximal non-electrochemically active region and the distal region 205 is an electrochemically active region. FIG. 2B shows a side schematic view of a variation of a probe electrode including a medial heterofunctional region 207 that forms a hydrophobic annular separation between the distal electrochemically active region 205 and the proximal non-electrochemically active region 203.

In the example shown in FIGS. 2A and 2B, the dimensions shown are merely illustrative, and may be varied. For example, in FIGS. 2A and 2B, the diameter of the post region of the probe, d, is illustrated as less than 2 μm. In some variations, the diameter may be between about 50 nm and 2 μm (e.g., about 500 nm, etc.). In FIGS. 2A and 2B, the post is shown as a cylindrical post that is proud of the base region (e.g., projecting approximately 90° from the base). In some variations the shape may be different. For example, the post may be hollow (tubular) or may be tapered (e.g., pyramidal, etc.). Other cross-sectional dimensions may be included. In addition, the dimensions shown may be varied. For example, the distal electrochemically active region 205 may have a height of between about 20 nm and about 5 μm in some variations. In other variations the height may be greater or lesser than this range. In some variations the distal electrochemically active region is formed of a nanoporous material, so the entire volume of the region contacts with solution (e.g., cytoplasm of the cell in variations penetrating the cell membrane).

In some variations the proximal non-electrochemically active region 203 may be taller or shorter than the distal electrochemically active region 205; in other variations the proximal non-electrochemically active region 203 is the same height as the distal electrochemically active region 205, as shown in FIG. 1A.

The distal electrochemically active region may electrically couple with the cell so that electrical recordings (and/or stimulation) may be applied to the cell. In general, the distal electrochemically active region 205 may capacitively couple with the cell or it may faradically couple with the cell. The electrochemically active region may generally perform both capacitive (e.g., non-faradiac) coupling to the solution, or pass faradiac current. In some variations this region has a high conductance value, e.g., >1 milliCoulomb per $cm^2$, though it may also be much lower (e.g., 1 microC/$cm^2$). As used herein the electrochemically active region is a region that is able to pass current with applied voltage either through faradiac or capacitive mechanisms. This region may electrochemically pass current (positive or negative current) between the solution and the electrode itself.

The distal electrochemically active region may be formed of any appropriate material, including one or more of Pt, PtO, Ir, IrO, $Ir_2O_3$, $IrO_2$, Ru, RuO, Au, Co, graphite, etc., including other materials that allow a relatively high current density. In general the material may be conductive, non-toxic to the cells, and is typically hydrophilic.

Figure 2C:
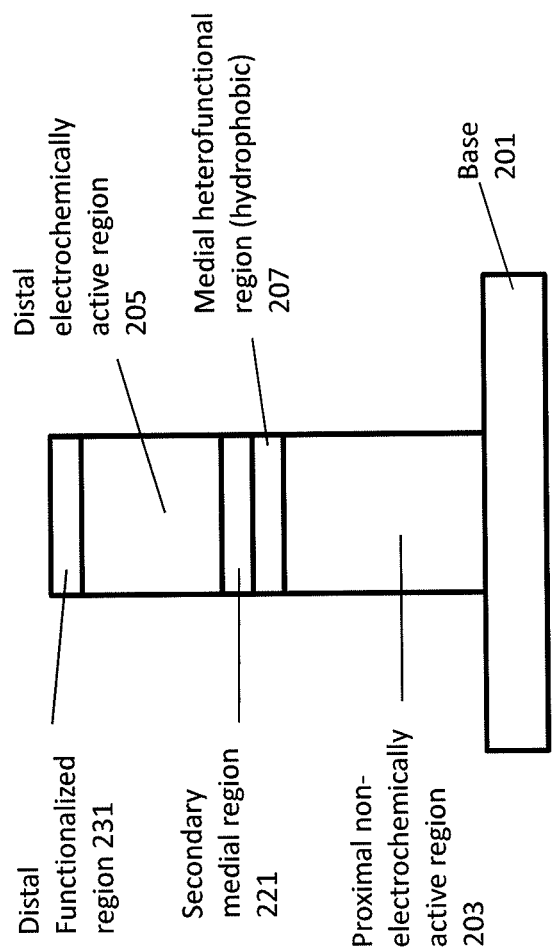
FIG. 2C is a schematic side view of another variation of a multi-functional heterometallic probe.
Figure 2D:
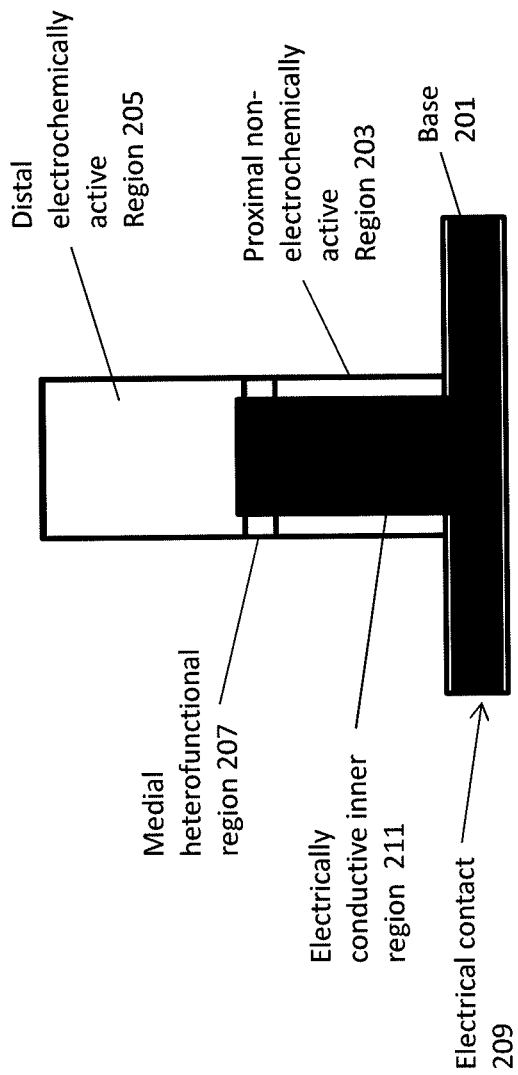
FIG. 2D shows a cross-section though one variation of a probe electrode such as the one shown in FIG. 2B.

The distal electrochemically active region 205 may be coupled to an electrical contact in the base through an electrical connection that passes through the non-electrochemically active region 203. In some variations this connection is a simple physical connection between the distal electrochemically active region and the electrical contact. An example of this is shown in FIG. 2D, which illustrates an exemplary section through one variation of a transmembrane probe, such as the example shown in FIG. 2B. In FIG. 2C, the distal electrochemically active region 205 is shown in contact with an electrical conductor 211. The electrical conductor is within (and passes thorough) the proximal electrochemically active region 203 on the way to an electrical contact 209, shown in FIG. 2D on the side of a region of the base 201. The electrical contact may be located anywhere on the base, including the bottom, top, side or some combination thereof. The base may be formed on or as part of a chip or other substrate, and may be formed integral with or separate from the base.

In any of these examples, the proximal non-electrochemically active region may include an outer insulative coating. In some variations the proximal non-electrochemically active region is continuous with the base (e.g., formed of the same material).

The proximal non-electrochemically active region electrically insulates the proximal portion of the probe electrode to prevent any electrical current passing from this that region. The proximal non-electrochemically active region (and also the base) may be formed of any appropriate material that is not electrochemically active. Typical examples may include $SiO_2$, $Al_2O_3$, some polymers, etc. As mentioned, these materials are insulators and are all non-reactive. In general the proximal non-electrochemically active region has a core that is electrically conductive (to allow coupling of the distal electrochemically active region with an electrical contact in or beyond the base) and the outside of the proximal non-electrochemically active region must act as an insulator. This outer region of the proximal non-electrochemically active region may be relatively thin (e.g., less than 1 nm thick) but surrounds and insulates the inner conductive core.

The inner conductive core of the proximal non-electrochemically active region is generally formed of a material that is conductive and that doesn't react with the distal electrochemically reactive region. For example, the inner conductive core and the distal electrochemically active region should not form a reactive metal combination, but should form a low-resistivity (e.g., Ohmic) contact. As mentioned above, the outer region (which may be a layer, coating, cladding, or the like) of the proximal non-electrochemically active region is typically hydrophilic.

The base region 201 in any of the variations described herein may be very similar to the proximal non-electrochemically active region. In general, the base region may provide an electrical connection between the distal electrochemically active region and a contact. In some variations the electrical contact may be formed on or integral with the base region. The base region may act as a substrate for forming the post region of the probe in some variations. The base may support the post region and may include additional structures, including electronics (e.g., amplifiers, preamplifiers, and the like) to assist in signal processing and/or transmission of any signal from the distal electrochemically active region 205 and an additional computer/digital device that may process, transmit and/or record signal from the probe. For example, in some variations the base and post may be formed as part of a chip, including one or more printed circuit board components (PCBs). The base region is also typically hydrophilic.

For convenience, the region of the probe projecting from the base is referred to as a "post." As mentioned above, this post region may be configured to have any appropriate shape (e.g., cross-sectional shape), for example, it may be cylindrical, conical, tubular (e.g., hollow), or the like, and may have an irregular or non-uniform cross-sections, or non-circular/non-elliptical cross-sections (rectangular, square, etc.). In some variations some region or regions of the post include a recessed region (e.g., cavity).

Returning now to FIG. 2B, in some variations of the nanoscale probes described herein the probe includes a medial heterofunctional region 207 that is configured to provide or form a hydrophobic band or region along the length of the probe (between regions that are substantially less hydrophobic). In some variations the height of this region is approximately or less than about 100 nm. For example, the height is between about 2 nm and about 25 nm (e.g., between about 2 nm and about 15 nm, between about 5 nm and about 10 nm, between 10 nm and 25 nm, less than 10 nm, etc.).

In FIG. 2B the medial heterofunctional region forms an annular ring or band around the outer perimeter of the post. In some variations the medial heterofunctional region is a complete ring; in other variations the medial heterofunctional region is a partial or broken ring.

In general, the medial heterofunctional region presents an outer face that is at least moderately hydrophobic. Thus the medial heterofunctional region forms a hydrophobic region along the length of the post between two hydrophilic regions (in FIG. 2B, the distal electrochemically active region and the proximal non-electrochemically active region). Thus, the medial heterofunctional region may be understood to be a region of hydrophobicity distinct from the upper and lower regions surrounding it on the probe.

Figure 2E:
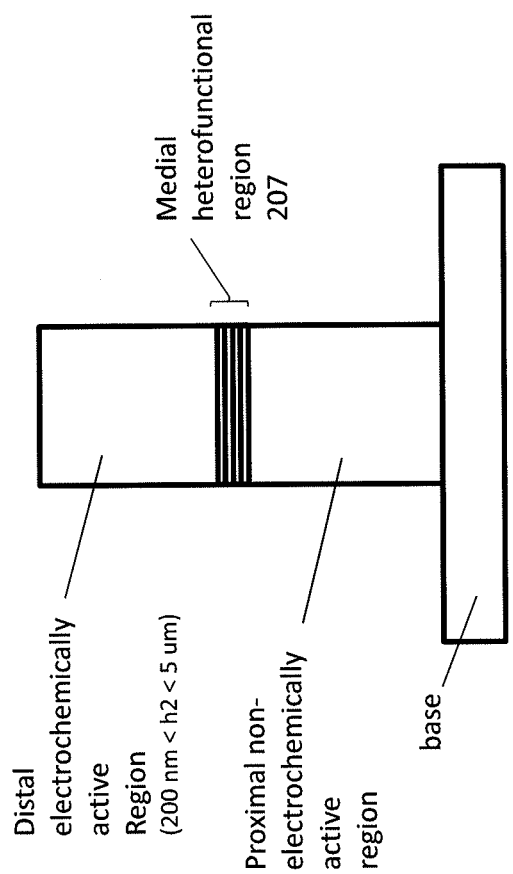
FIG. 2E shows a schematic side view of another variation of a probe electrode having a striated medial heterofunctional region for fusing within a lipid bilayer.

In some variations, such as the example shown in FIG. 2E, the medial heterofunctional region 207 is formed of multiple regions (or bands) of hydrophobicity (e.g., between about 5-10 nm each). These bands (e.g., the width of the bands) may approximately match the diameter of a cell membrane. The overall width or length of the medial heterofunctional region in this example may be between about 25 and 200 nm, or up to 1 μm.

Examples of probes, including methods of fabricating and using the probes, are provided below in the examples (e.g., Examples 1-3), which also characterize specific examples of probes.

The medial heterofunctional region 207 may be formed of any appropriate material(s). In some variations the medial heterofunctional region is formed of a material to which molecules having or presenting hydrophobic properties or regions may self-assemble. For example, the medial heterofunctional region may be formed of a metal (e.g., gold, nickel) onto which a hydrophobic molecule (e.g., proteins and organic molecules, polymers, etc.) may be attached. The attachment may be self-assembling or it may be formed. In some variations the medial heterofunctional region is formed directly of a hydrophobic polymer or other material.

In addition to the distal and proximal regions described above, other distal and proximal regions may be used. In general, these distal and proximal regions may be formed of a material that is more hydrophilic than the medial heterofunctional region. For example, in some variations the probe is not an electrical probe, but may still be configured to form a long-lasting and non-destructive seal with the cell. The distal region of the probe may be a hydrophobic region that has been otherwise functionalized to include a marker or probe for use with the cell.

Any of the probe variations described herein may include additional regions, such as additional functionalized regions. For example, in some variations a region of the probe, typically (though not exclusively) at or near the distal end of the probe may be configured to provide a functionalized region. A functional region may include another material on the probe (e.g., in some variations on top of the electrochemically active region) surface that can support different molecules, particles, drugs, etc. For example, in some variations the functionalized region includes one or more functional markers such as calcium markers, enzymatic markers, or the like. Markers may include visual indicators, including fluorescent molecules, and may be configured to bind to specific cellular components (e.g., using antibodies, siRNA, etc.). The functionalized region is typically located distally of the medial heterofunctional region. In some variations the functionalized region may be referred to as a distal functionalized region. The functionalized region may include a component (e.g., molecule, such as a drug, marker, buffer, etc.) that is either retained on the probe, or released within the cell. Thus, in principle a functional region may be configured to include virtually any material that is intended for placement or release within the cell.

In some variations the probe may, in addition to the medial heterofunctional region, include a secondary heterofunctional region, which may also be referred to as a secondary medial region. The secondary medial heterofunctional region may be a second hydrophobic region and may be configured similarly to the medial heterofunctional region. In some variations the secondary heterofunctional region may be a region where the hydrophobicity is tuned to a desired value independent of the medial heterofunctional region or the other hydrophilic regions. Thus, the material forming the secondary medial region is different from the materials forming the medial heterofunctional region.

In operation, a secondary medial region may be used to bind to specific regions within the cell, such as the nucleus or other organelles. For example, the secondary medial region may include nuclear-targeting proteins (e.g., nucleolin) for preferentially binding to a cell nucleus.

FIG. 2C illustrates one version of a probe including a base 201, a proximal non-electrochemically active region 203, a medial heterofunctional region that is hydrophobic 207, and a distal electrochemically active region 205. In addition, a secondary medial region 221 is also included; in this example the secondary medial region is positioned just distal to the medial heterofunctional region 207. As discussed above, this secondary medial region may be positioned virtually anywhere on the probe, including more distal regions. In FIG. 2C, the probe also includes a distal functionalized region 231.

Additional examples of probes, including probe electrodes, methods of making probes, and characterizations of probes are provided in Examples 1-3 below. Unless otherwise indicated, these examples illustrate one or more variations and are not intended to be limiting. In particular, dimensions, values, and measurements provided in these examples may represent approximate values and may be varied without parting from the scope of the invention as provided herein.

EXAMPLE 1

Figures 3A, 3B, 3C, 3D:
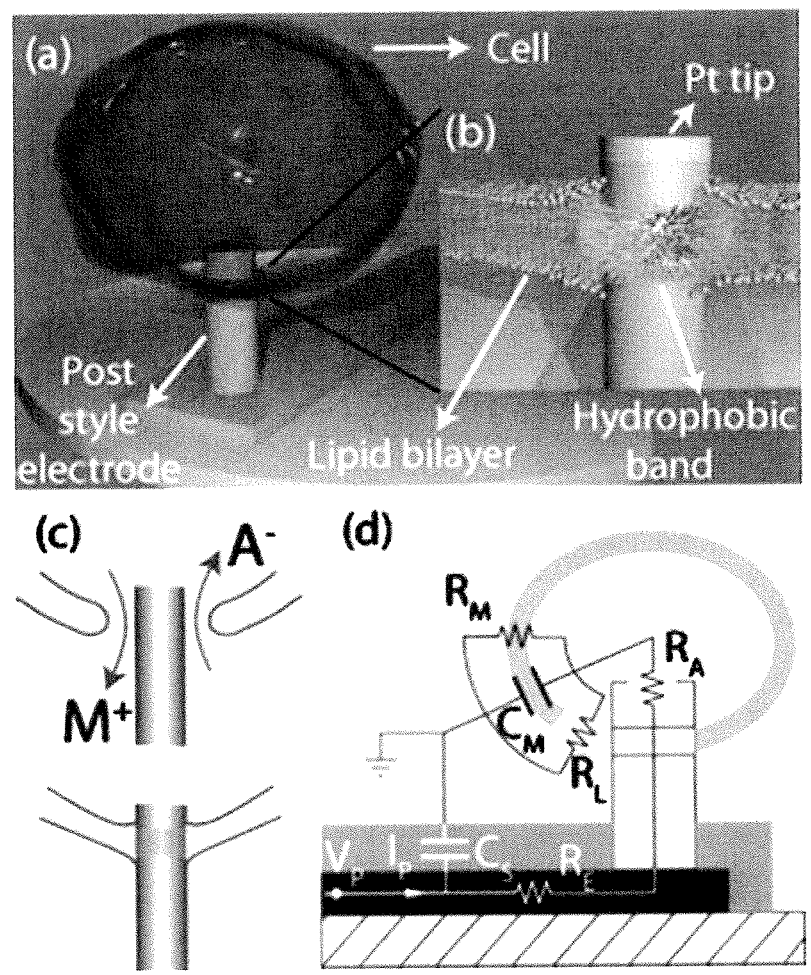
FIG. 3A is a schematic showing nanoscale probe (referred to in some variations as a "stealth probe") fused with a cell membrane, allowing direct electrical access into the cell.
FIG. 3B shows a magnified view of an interface between a probe and cell membrane.
FIG. 3C (top) shows a thin hydration layer that exists between probes with uniform surface chemistry and the membrane allowing ion leakage (similar to that shown in FIG. 1D). The bottom of FIG. 3C shows a ("stealth") probe as described herein fused with the cell membrane forming a tight gigaohm seal.
FIG. 3D illustrates an equivalent electrical circuit of a cell fused onto a stealth probe.

Here we present a chip-based device including a plurality of nanoscale probe electrodes formed as solid-state metallic nanoscale electrodes that spontaneously fuse with the cell membrane to form gigaohm seals. Instead of relying upon destructive formation of membrane holes and serendipitous surface adhesion, these metallic electrodes spontaneously insert into the hydrophobic membrane core by mimicking the hydrophobic banding of transmembrane proteins, forming a well-defined bioinorganic lateral junction. For example, FIG. 3A-3B schematically illustrates attachment of a cell to the probe electrodes described herein. These "stealth" probes consist of hydrophilic posts with a 5-10 nm hydrophobic band (medial heterofunctional region) formed by molecular self-assembly onto the exposed edge of a Au layer. Due to hydrophobic interactions between the band and the lipid membrane core, a tight interface impermeable to polar molecules and charged ions is formed between the probe and the membrane. With mounting evidence of cell viability despite penetration by nanostructures, such an engineered interface may provide long-term high-quality electrical recording from cells. This is distinct from uniform surface modification, where either the lipid's hydrophilic headgroups or hydrophobic core will have unfavorable interactions with the surface, leading to a thin hydration layer (e.g., see FIG. 3C, top) and poor seal resistance. These stealth probes have strong mechanical adhesion within model lipid membranes, however it was unknown whether these would also form high-electrical resistance seals.

To test the electrical seal resistance, Pt-tipped stealth probes were fabricated onto metal electrodes and the change in electrochemical resistance measured as the post fused to a red blood cell. The equivalent electrical circuit for this device is shown in FIG. 3D. The critical requirements are an exposed 5 nm hydrophobic band to cause membrane fusion, low-resistance electrical access to the tip of the stealth probe for redox-induced current injection into the cell, and highly insulated electrodes outside the cell to eliminate electrical leakage and lower capacitance.

Figures 4A, 4B, 4C, 4D, 4E, 4F, 4G:
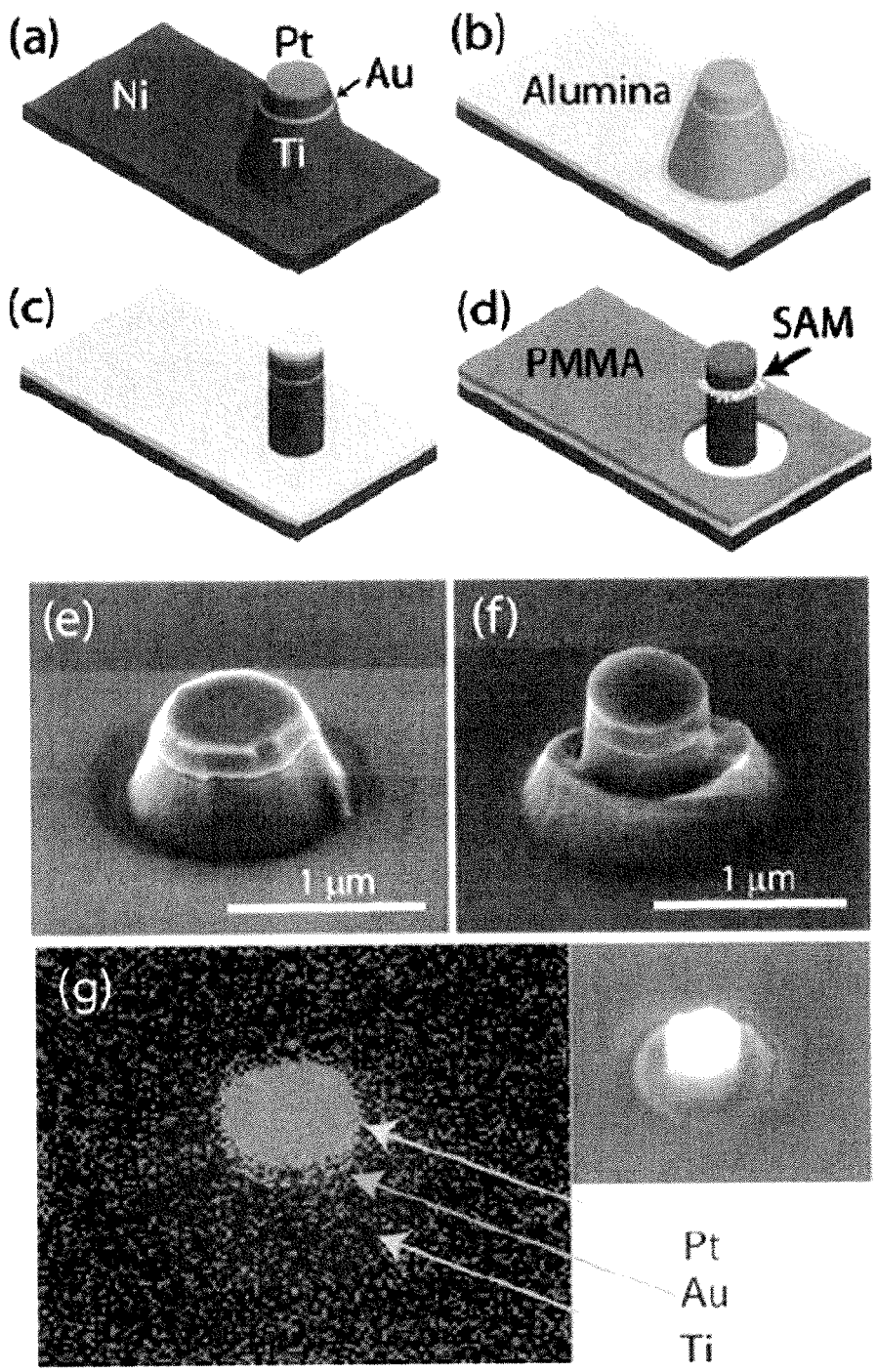
FIGS. 4A-G illustrates fabrication of one variation of a probe electrode as described herein.

Metallic stealth probes were fabricated onto larger bottom electrodes according to the procedure shown in FIGS. 4A-G. The 10 μm-wide nickel bottom electrodes were patterned onto a 200 nm thermal oxide Si substrate using e-beam lithography, Ni evaporation and lift-off. Next, the stealth probe was defined by e-beam writing a 1 μm diameter opening in a bilayer resist of 800/200 nm thick 495/950 k molecular weight polymethyl methacrylate (PMMA). The probe was formed by sequential e-beam deposition of 500 nm Ti, 5 nm Au for hydrophobic functionalization, 10 nm Ti, and 10 nm Pt for electrochemical activity. After PMMA lift-off, the device was oxygen plasma cleaned for 10 min to passivate the exposed lateral surface of the posts and the bottom electrode. A second passivation of 10±1 nm thick alumina was subsequently deposited using atomic layer deposition at 150° C. (FIG. 4B).

After alumina passivation of the post, the sidewalls were covered with alumina and the gold band was not exposed and rough (see FIG. 4E). To obtain a clean gold band and reduce posts to the desired size (approximately 400 nm), the sidewalls of the post were milled using a focused ion beam (FIB) (see, e.g., FIGS. 4C to 4F). The alumina on the platinum electrode was selectively removed to increase electrochemical activity by spin coating a PMMA resist, e-beam writing a hole on top of the post, and wet etching with 10% potassium ferricyanide, 20% potassium hydroxide in water. Auger spectroscopy of the probe shows clean Pt, Au, and Ti surfaces on the probe (FIG. 4G). A 1 µm thick layer of PMMA was then homogenously spin coated and e-beam patterned to expose only the approximately 600 nm tall post to reduce electrode capacitance (FIG. 4D). The stealth probe devices were completed by immersing in a 10 mM butanethiol solution in deionized water for 3 h to hydrophobically functionalize the gold band, followed by rinsing with deionized water and blown drying with $N_2$.

The probe's electrochemical activity was tested by cyclic voltammetry in a 0.1 M KCl solution containing equal concentrations (5 mM) of $K_4Fe(CN)_6$ and $K_3Fe(CN)_6$ using a 1 mm thick platinum wire counter electrode. In a typical experiment, the voltage was swept at 0.1 V/s from −200 mV to 200 mV using a patch clamp amplifier, and the current recorded after filtering at 1 kHz. The current response of a single post electrode is shown in FIG. 5 ("without cell" traces). For the 12 devices tested in this study, the maximum current varied between approximately 100 pA to 1 nA, however, the current remained constant over a period of days for each individual device. These values agree well with the 500 pA current expected from an ideal 400 nm disk electrode under these conditions, indicating the 1.6±1 GΩ, resistance is dominated by the electrochemical resistance at the post tip ($R_A$ in FIG. 3D), with minimal leakage. The capacitance was consistently in the range of 260±70 pF based on the current hysteresis (not shown for clarity).

Figures 5A, 5B:
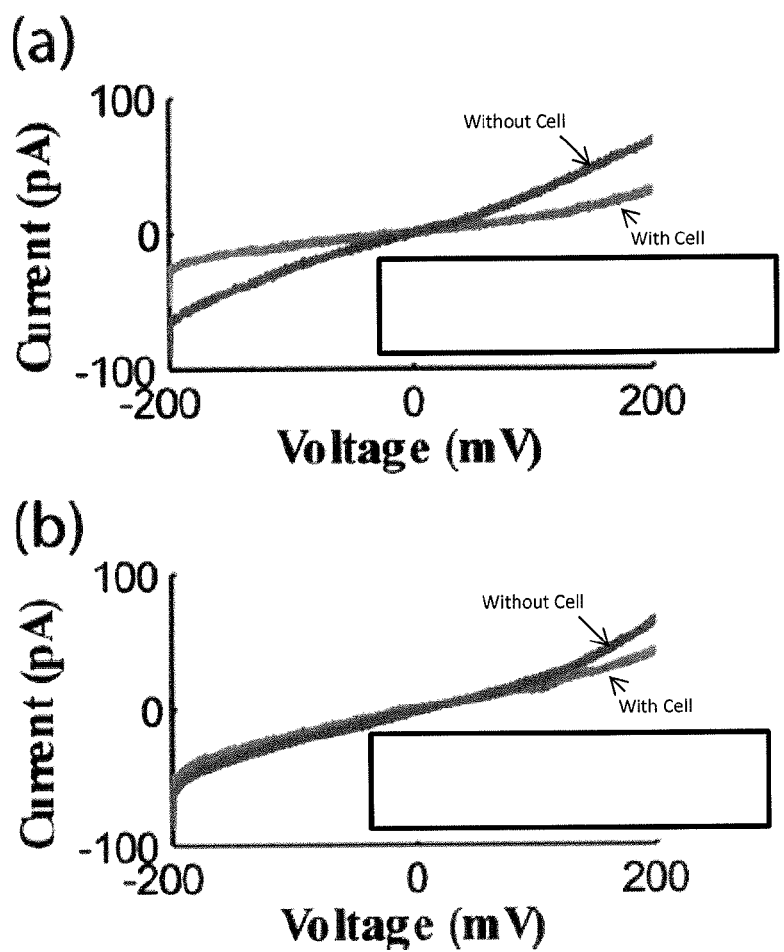
FIGS. 5A and 5B show cyclic voltammetry of a single stealth probe at 0.1 V/s in 0.1 M KCl solution containing 5 mM $K_4Fe(CN)_6$ and $K_3Fe(CN)_6$.
Figure 6:
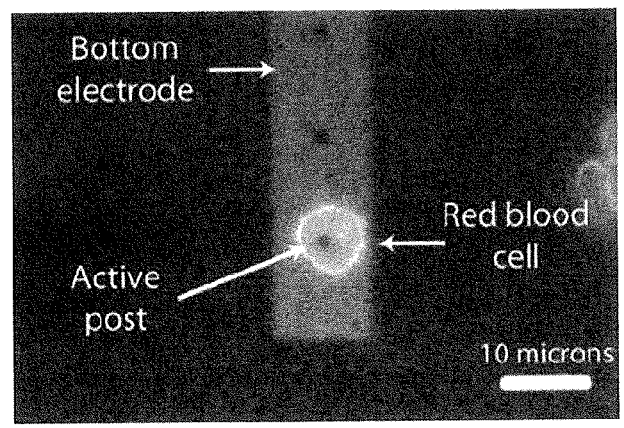
FIG. 6 shows an epifluorescence micrograph of a red blood cell patched by a stealth probe. The cell spontaneously adhered to the post, and did not dislodge once in contact. Multiple posts (dark circles) are fabricated on the same electrode, however all but the active one are passivated with 1 μm of PMMA.

The stealth probe-cell seal quality was tested using human red blood cells whose membranes had been tagged using 10 µM Texas red dye in 0.9% NaCl for visualization. Red blood cells were brought into contact with the posts using a pipette micromanipulator, where they became attached (FIG. 6). For posts functionalized with butanethiol, the electrochemical current immediately decreased significantly, indicating a high-resistance seal had formed (FIG. 5A). The corresponding seal resistance was 3.8±1.9 GΩ, with a maximum of 5.4 GΩ over 5 trials, fulfilling the requirement for high-quality patch clamp seals and surpassing other chip-based seals which typically lie in the range of 100 MΩ to 2 GΩ. The gigaohm seal formation yield was high; however repeated testing without cleaning degraded the device. The fact that the resistance is not as high as pristine bilayers (10-100 GΩ) suggests that improvements to the post/membrane interface may further increase seal resistance.

Probes without the functionalized hydrophobic band did not form high resistance seals. Upon cell contact with probes that were identical except without butanethiol functionalization, a small reduction in current can be observed (FIG. 5B), corresponding to a resistance increase of approximately 700 MΩ. Increased resistance solely due to surface contact between the cell membrane and the functionalized probe can also be ruled out. Assuming that the cell membrane is in conformal contact with the top 200 nm of the post (where the post has a shoulder, FIG. 5F), the resistance should be approximately 800 MΩ based on measurements of the ionic conductivity between model lipid bilayers and clean substrates. This is remarkably close to the approximately 700 MΩ measured for unfunctionalized probes but much less than the 3.8 GΩ for functionalized ones. An increase of 4 GΩ would require conformal contact over a 12 µm diameter disk, which clearly did not occur for the 6-8 µm red blood cells studied here. The stealth probe architecture thus provides a nondestructive means to directly access the cell interior while maintaining a high resistance seal at the membrane interface. Fusion into the hydrophobic membrane core is a critical step toward forming interfaces without relying on cell-specific surface protein coatings or charge interactions, which often limit the cell types amenable to patch clamping. This design can be readily extended to large on-chip arrays of stealth probes which could provide multiple patches to an individual cell, or single patches to a large number of cells simultaneously. Since the probe does not open holes in the membrane or cause cytosolic leakage cells may be viable for longer periods, enabling both fundamental biochemical studies and technological applications.

EXAMPLE 2

As mentioned above, some variation of nanoscale probes may include a medial heterofunctional region that is more hydrophobic than adjacent regions on the probe and allow for insertion of the probe into the lipid membrane. Here we demonstrate that by replicating the nanometer-scale hydrophilic-hydrophobic-hydrophilic architecture of transmembrane proteins in an artificial nanoscale probe, the probe can be made to spontaneously insert and anchor within the lipid bilayer core, forming a high-strength interface. These nanometer-scale hydrophobic bands are fabricated on metallic probes by functionalizing the exposed sidewall of an ultrathin evaporated Au metal layer rather than by lithography. Penetration and adhesion forces for butanethiol and dodecanethiol functionalized probes were directly measured using atomic force microscopy (AFM) on thick stacks of lipid bilayers to eliminate substrate effects. The penetration dynamics were starkly different for hydrophobic versus hydrophilic probes. Both 5- and 10 nm thick hydrophobically functionalized probes naturally resided within the lipid core, while hydrophilic probes remained in the aqueous region. Surprisingly, the barrier to probe penetration with short butanethiol chains ($E_{o;5}$ nm=21.8 $k_bT$, $E_{o;10}$ nm=15.3 $k_bT$) was dramatically higher than longer dodecanethiol chains ($E_{o;5}$ nm=14.0 $k_bT$, $E_{o;10}$ nm=10.9 $k_bT$), indicating that molecular mobility and orientation also play a role in addition to hydrophobicity in determining interface stability. Thus, in some variations, the medial heterofunctional region (e.g., the hydrophobic band or bands) of a nanoscale probe may be formed to have dimensional mimicking the thickness of the cell membranes into which the probe is to be inserted. In addition, the method of functionalizing the medial heterofuncitonal region (forming the hydrophobic band) may be optimized by selection of materials, including, e.g., the hydrophobic molecules. In some variations, the portion of the medial heterofunctional region (e.g., the hydrophobic material) may comprise different length alkanes.

Ideally, interaction between a probe and the bilayer interior could be achieved by modifying the material's surface characteristics. A necessary trait of these "artificial membrane proteins" is the capacity to specifically insert into the bilayer core and form a strong interface, mimicking endogenous transmembrane proteins. A broad variety of molecular functionalizing agents are available, including small molecules, peptides, and polymers. Peptide interactions with the hydrophobic membrane core have been studied at length and are generally well-described by an empirical hydrophobicity scale. However, these thermodynamic guidelines provide little insight into the protein-lipid dynamics important for kinetic processes such as bilayer penetration. Other characteristics of molecular agents such as entropy, crystallinity, orientation, and spatial patterning may also play important roles and enable property tuning beyond what is currently available with proteins. Here we present a simple microfabricated architecture based on metallic multilayer probes that allows probe fusion into a lipid bilayer core and systematic control of lateral bilayer-material interactions (FIG. 7A-D). The probes in this example consist of a metallic post with a thin, 2-10 nm hydrophobic band (medial heterofunctional region) that is designed to fuse into the core of the lipid bilayer. These probes are designed to mimic two transmembrane protein characteristics: The transmembrane regions are mostly hydrophobic with hydrophilic groups on either side, and the thickness of the hydrophobic domain should be commensurate with the bilayer thickness. These characteristics are extremely encouraging for engineered biomimetic systems, because no special protein interactions or molecular-scale configurations are necessary. Instead, creating an approximately 3 to 5 nanometer hydrophobic band on an otherwise hydrophilic structure is the critical design feature.

Figures 7A, 7B, 7C, 7D:
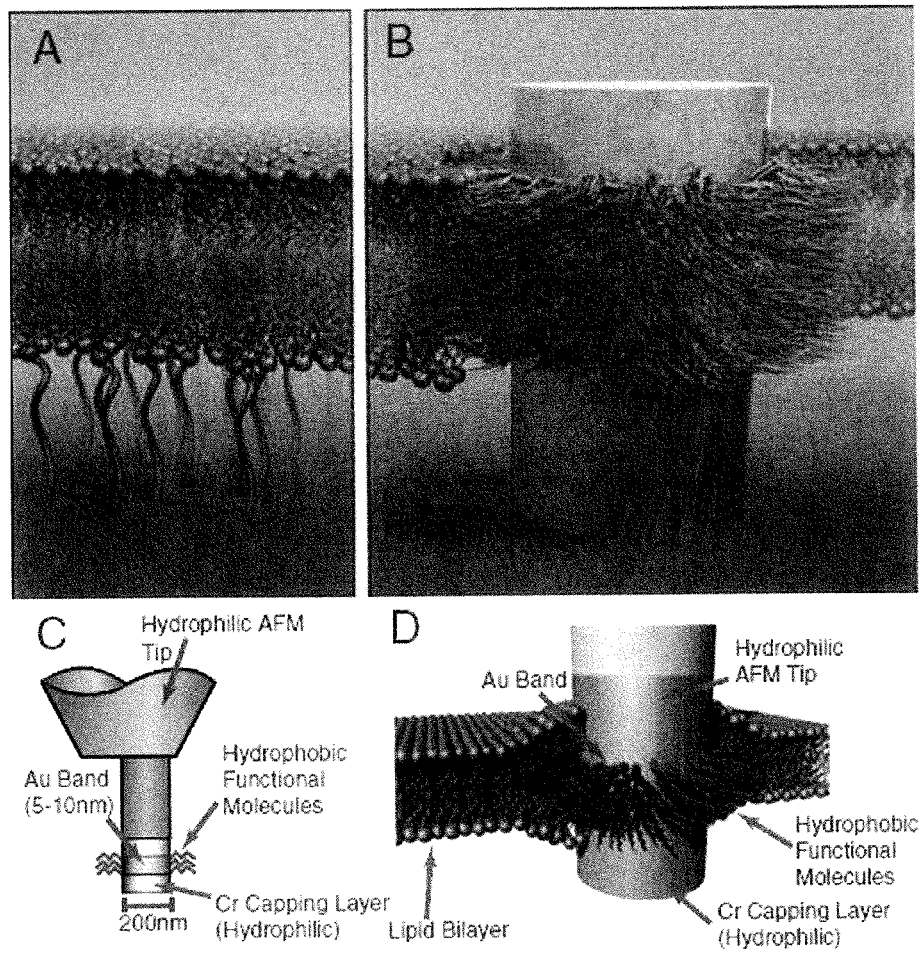
FIGS. 7A-7D illustrate diagrams of one variation of a probe electrode ("stealth probe") being integrated with a lipid bilayer.

Lithographically defining 3-5 nm features on nonplanar structures (such as a cylindrical probe) is beyond even state-of-the-art lithography equipment. However, hydrophobic bands of these dimensions can be readily formed by molecularly functionalizing the exposed sidewall of an evaporated metal layer. For example, FIG. 7C shows a schematic of a probe (formed at the end of an AFM tip) that uses self-assembly of hydrophobic molecules on the edge of an Au layer that is sandwiched between hydrophilic metals. The height of the functional band is determined by the thickness of the Au, which can be controlled to 1-2 nm using current electron-beam evaporation or sputtering techniques. This technique provides a flexible platform to examine how both architecture and various molecular agents influence adhesion within the bilayer itself and could be integrated into a number of biointerface systems, such as deep brain implants, neural prosthetics, and patch-clamp devices. As mentioned above, we use atomic force microscopy (AFM) to directly measure the location, penetration force, and adhesion strength of stealth probes functionalized with different molecular fusion agents within the bilayer. Previous studies have found that AFM is an excellent tool to measure bilayer thickness, force penetration barriers, and the effects of homogeneous tip functionalization. In addition, we find that the dynamic characteristics of AFM penetration through a series of bilayers reveal the preferential probe localization within a bilayer. The adhesion force of different probe functionalities was measured from the probe retraction force from the bilayer, and it was discovered that different length alkanes had significantly different adhesion strengths despite very similar hydrophobicities. These measurements show that the stealth probe architecture is a straightforward means to control integration and penetration of inorganic microstructures into lipid bilayers and may provide a flexible platform for nondestructive integration into cells.

MATERIALS AND METHODS

Figures 8A, 8B, 8C, 8D, 8E, 8F, 8G, 8H, 8I, 8J:
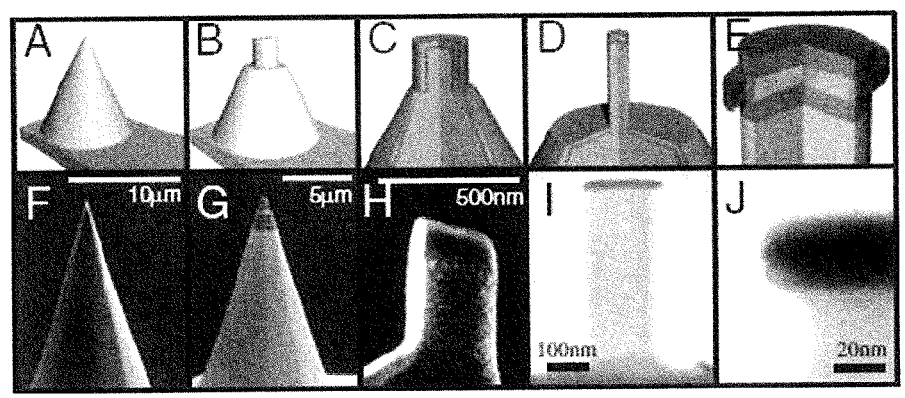
FIGS. 8A-8J shows atomic force microscopy (AFM) post probe fabrication.

The probes examined in this example were formed using standard commercial AFM cantilevers having a nominal spring constant of 0.08 N/m. The tips of the cantilevers were formed to mimic the probe design (and particularly the post configuration) that may be used in variations of the probes described herein. AFM cantilevers were mounted vertically in a focused ion beam microscope (FIB). The tips were milled to a post shape approximately 500 nm in diameter and 600 nm long using a 30 kV, 10 pA Ga-beam, followed by a 90° rotation onto their sides and subsequent milling to complete the post geometry (see, e.g., FIGS. 8B and 8G). A layered Cr—Au—Cr structure (each Cr metal layer=10 nm thick, Au layer=5 or 10 nm) was deposited by e-beam metal evaporation on the modified AFM cantilevers at a rate of 0.5 Å/s (FIGS. 8C and 8H). Thicknesses are ±5% and were calibrated using x-ray reflectivity. Following metal deposition, the cantilevers were remilled in the FIB to a final diameter of approximately 200 nm using the same milling procedure, with the exception of the beam current being reduced to 1 pA (FIGS. 8D and 8I).

For this example, probes were tested in stacks of lipid bilayers. Stacks of 30-2000 lipid bilayers were fowled by gentle hydration of a dried lipid cake. Glass coverslips (25 mm dia.) were cleaned for 30 min in Piranha etch. Coverslips were then rinsed thoroughly with deionized water and dried under nitrogen. Ten microliter drops of 10 mg/mL of a 2:1 1-stearoyl-2-oleoyl-sn-glycero-3-phosphocholine (SOPC) and cholesterol (Avanti Polar Lipids) solution in chloroform were deposited on the clean coverslips, dried under a stream of nitrogen, and desiccated under vacuum for at least 4 hrs. Desiccated coverslips were mounted in a closed fluid cell. A strip of PTFE was used to manually spread the dried lipid over the coverslip into a thin layer. Following spreading, 1 mL of 1.6% NaCl solution was added to the fluid cell and allowed to sit for approximately 2 h.

Membrane probes were functionalized for at least 12 hrs in 5 mM ethanolic solutions of either 1-butanethiol or 1-dodecanethiol. Previously used tips could be refunctionalized with different molecules following a 30-min UV-ozone cleaning. After UV-ozone treatment, tips were soaked in pure ethanol for 30 min to remove any gold oxide. Functionalized membrane probes were removed from solution, rinsed in ethanol, and mounted in an Asylum Research MFP-3D AFM. Spring constant calibration was done using the Sader and thermal methods. Stack penetration testing was performed at 500 nm/s, while adhesion force testing was performed at a rate of 2 μm/s. A dwell of 1 sec was used between extension and retraction, when the probe is in contact with the bilayers to allow for fusion to occur. Force-clamp curves were obtained by initially bringing the probes into contact with a lipid stack at a rate of 4 μm/s. Loading was stopped when a force set point of 40-100 nN was reached. Once the set point was obtained, a 30-60 s dwell was triggered where the cantilever position was held constant. During this dwell session, the change in cantilever deflection was measured. Drift in the system was accounted for by leveling the low force/long time drift of the baseline.

As mentioned above, the post region of a stealth probe was fabricated directly upon silicon AFM tips in order to measure the probe force and displacement during probe penetration through a lipid bilayer as shown in FIG. 8A-8J. Initially, conical Si cantilever tips are milled into a roughly 500 nm diameter cylinder in a focused ion beam microscope (FIB) (FIGS. 8B and 8G). The cantilevers are then transferred to an electronbeam metal evaporator and layered Cr—Au—Cr stacks of either 10-5-10 nm or 10-10-10±0.5 nm are deposited. After metal deposition, the post sidewalls have a thin covering of Cr (FIGS. 8C and 8H) that inhibits self-assembly onto the gold layer. A second FIB milling is performed to remove the sidewall deposition and reduce the post diameter to approximately 200 nm, exposing the edges of the individual metal layers.

Transmission electron microscopy (TEM) confirmed the Au layer has a clean sidewall free of Cr (FIGS. 8I and 8J). The Au edge was then functionalized by self-assembly in 5 mM butanethiol or dodecanethiol solutions in ethanol for 12 h, rinsed with ethanol, and blown dry. To ensure this treatment did not functionalize the Cr layer we measured the contact angles of planar Cr films after immersion in the alkane thiol solutions, which were uniformly hydrophilic with a water contact angle <20°. Planar Au surfaces had contact angles of 110° and 110.5° for butanethiol and dodecanethiol, respectively.

Similar stealth probes could also be fabricated on Si wafers by e-beam lithography to define the post, followed by metal stack evaporation and lift-off. Butanethiol and dodecanethiol were chosen as hydrophobic functionalizing agents in this example to examine how molecular hydrophobicity and mobility influenced the probe-lipid interface. Butanethiol has a short, 4-carbon chain with high surface mobility on Au films, while dodecanethiol has a 12-carbon chain that forms crystalline monolayers. The hydrophobicity of these two species are similar (110° and 110.5°, respectively), but planar dodecanethiol monolayers are crystalline, while the liquid-like butanethiol monolayers adopt more random conformations.

Thus, the probes formed on the AFM tips described in this example may be similar or identical in any aspect (e.g., in the size and configuration of the medial heterofunctional region) as any of the other variations described herein, including those formed as discussed in Examples 1 and 3.

These functionalized AFM tips were compared to control samples with unfunctionalized Cr probes, which were uniformly hydrophilic. The forces and dynamics of probe penetration through a lipid bilayer were measured by advancing the probe into a stack of lipid bilayers using an AFM in force-testing mode. Previous AFM lipid penetration tests have used one or a few bilayers supported on a solid surface. However, single or double supported bilayers are not ideal for examining penetration behavior because the stealth probe tip will come into contact with the underlying substrate. This issue was avoided by creating thick, pancake-like stacks of hundreds to thousands of bilayers, allowing penetration through a large number of membranes without probe-substrate interactions. The thick bilayer stacks used here also differ from previous lipid experiments that hydrated a subregion of a larger stacked membrane structure.

Figures 9A, 9B, 9C, 9D:
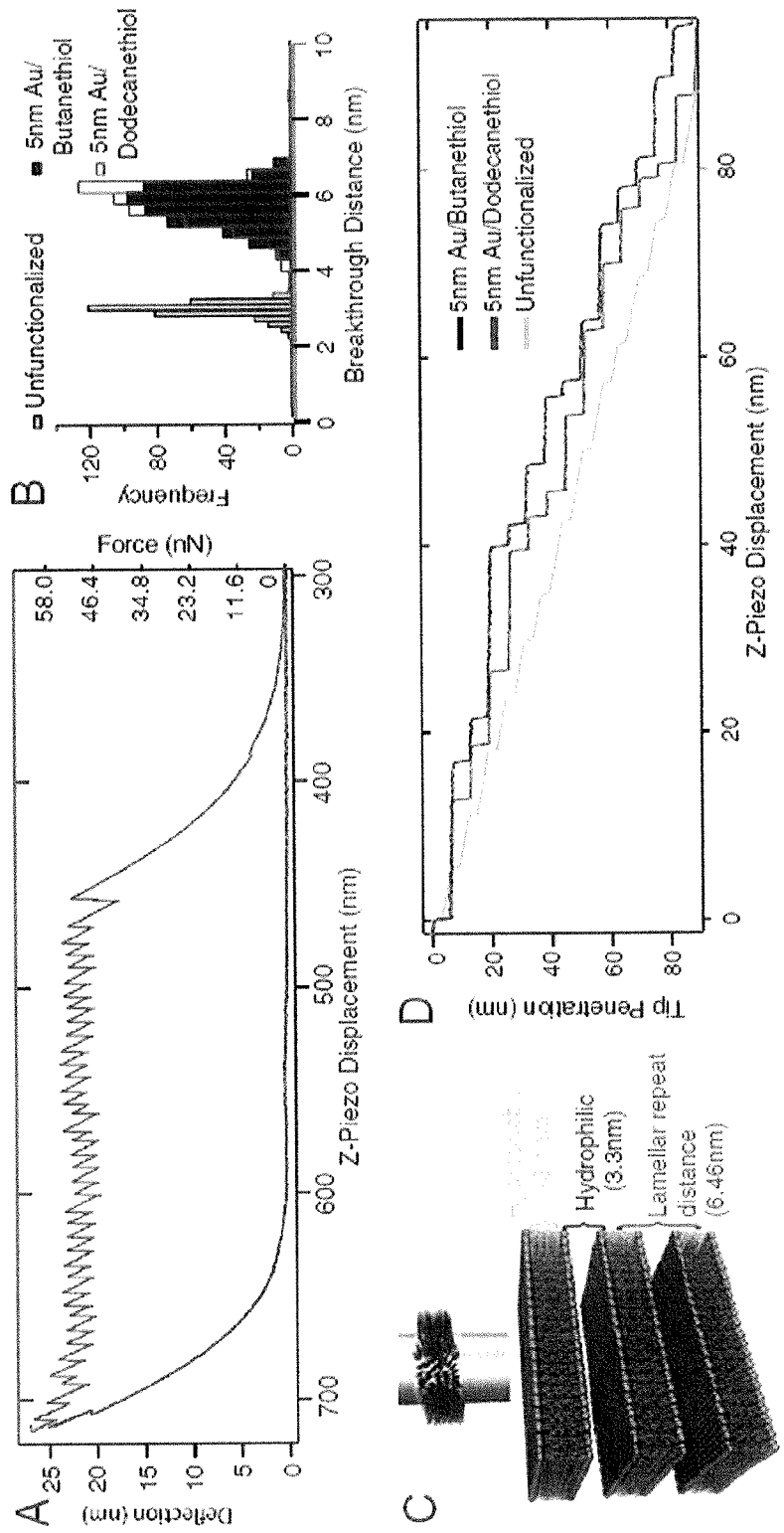
FIG. 9A is a representative AFM curve of penetration through a bilayer stack with an unfunctionalized probe (upper trace approach and lower trace withdrawal). Each of the 39 vertical drops corresponds to breaking through the hydrophobic core of a single lipid bilayer.
FIG. 9B shows histograms of stacked bilayer penetration distances for unfunctionalized, 5 nm Au/butanethiol, and 5 nm Au/dodecanethiol functionalized probes.
FIG. 9C is a schematic of breakthrough regions for each membrane probe. Hydrophilic, unfunctionalized probes breakthrough the hydrophobic bilayer core only, while hydrophobic functionalized probes jump from bilayer center to center.
FIG. 9D shows tip penetration behavior as a function of z-piezo displacement. Unfunctionalized probes have sharp jumps corresponding to breaking through the hydrophobic core, followed by relaxation through the hydrophilic region. Hydrophobic functionalized probes jump from hydrophobic core to hydrophobic core, with breakthrough distances corresponding to the lamellar repeat distance.

A force-displacement curve for penetration of an unfunctionalized hydrophilic tip through the top 39 bilayers of a stack is shown in FIG. 9A. Upon contact the stack is compressed an average of 16.9±6.7% (smooth approach curve from z=300 to 450 nm), until the applied force is sufficient to penetrate the bilayer, an average force of 58.3±3.0 nN at a loading rate of 3.6 nN/s. Each sawtooth deflection corresponds to the tip breaking through a single bilayer. The vertical step-height of each sawtooth corresponds to the distance the probe tip moves when breaking through the bilayer ("breakthrough distance"), while the failure force is the highest force value before rupture. The lipid stacks produce high-quality breakthrough data, as seen from the uniformity of the force and distance.

Surprisingly, we discovered that the breakthrough distance the tip moves after rupturing the bilayer is indicative of the probe's relative resting position within the bilayer. This is highly advantageous because traditional techniques such as optical microscopy, x-ray diffraction, or TEM cannot measure the position of an individual probe within the bilayer. Previous measurements with hydrophilic pyramidal AFM tips found that the breakthrough distance was equivalent to the thickness of the hydrophobic bilayer core, which acts as a barrier to penetration due to the interfacial energy of contact. In this case, the hydrophilic tip pushes against the top of the hydrophobic layer until enough force is applied to rupture the membrane, at which point the tip jumps through the hydrophobic core and stops at the aqueous headgroup region. Measurements with the hydrophilic control tips confirmed these results, with a breakthrough distance of 2.9±0.3 nm (FIG. 9B). This agrees quantitatively with the 3.1 nm hydrophobic core thickness of 2:1 SOPC:cholesterol bilayers as used here, including the bilayer compression before breakthrough. The hydrophilic probe thus normally resides within the hydrophilic gaps or membrane headgroups before penetration.

However, for hydrophobic stealth probes the band is expected to reside within the center of the bilayer to minimize interfacial energy. The breakthrough distance in this case should then equal the center-to-center distance between bilayers due to the band translating from the middle of one membrane to the next to avoid contact with the aqueous regions. Indeed, 5 nm Au bands functionalized with butanethiol or dodecanethiol give breakthrough distances of 5.6±0.6 nm and 5.7±0.6 nm, respectively (FIG. 9B), nearly double the hydrophilic result. The breakthrough histograms for these two molecules are extremely similar, indicating that both probe functionalizations reside in the same well-defined location. The breakthrough distances agree with the measured equilibrium lamellar spacing of 6.46 nm after accounting for the 16.7% compression of the bilayer stack, which reduces the expected spacing to 5.4±0.4 nm. The behavior of probes with 10 nm Au bands is similar to that of 5 nm Au bands, with breakthrough distances of 5.7±0.3 nm and 5.9±0.2 nm for butanethiol and dodecanethiol functionalizations, respectively. Thus, both 5- and 10-nm thick bands functionalized with butane and dodecane thiol reside in the middle of the hydrophobic bilayer core.

The most striking difference between hydrophobic and hydrophilic functionalized surfaces is revealed in the bilayer penetration dynamics (FIG. 9D). For the hydrophilic Cr probe the tip motion consists of short, abrupt 3 nm drops corresponding to membrane core penetration, followed by linear motion (FIG. 9D, bottom curve) as the AFM cantilever moves vertically through the bilayer stack. During the linear motion the force also increases linearly (FIG. 9A), and the total distance traversed before breakthrough is equal to the thickness of the hydration layer plus the headgroup thickness. We believe this results from the hydrophilic probe contacting the top of an unbroken bilayer and expelling the water layer beneath it as the probe is advanced. This causes the first two bilayers underneath the probe to be in close proximity right before rupture. Following breakthrough of the top bilayer, the probe is then immediately in contact with the next bilayer and the process repeats.

In contrast, both butanethiol and dodecanethiol stealth probes exhibit abrupt, 5-6 nm drops corresponding to membrane core to membrane core transitions, followed by extremely flat plateaus indicating very little motion within the bilayer with increasing force (FIG. 9D, middle and left most curves). For either functionalization, the average motion between breakthroughs was 0.2 nm, indicating the probes had a very strong affinity for the center of the bilayer. No intermediate states were observed during the breakthrough events, which might indicate metastable locations for the hydrophobic band. The dramatic difference between the two mechanisms enables facile identification of where the hydrophobic band naturally resides.

The adhesion strength of the probes within the bilayer was measured by a combination of the AFM force-displacement curves during probe withdrawal (FIGS. 10A-10C, bottom curves) and dynamic force-tests of penetration. Unfunctionalized tips (FIG. 10A) show lipid-tether formation as typically observed with hydrophilic probes, characterized by the multiple step-like failure events with zero-withdrawal force plateaus on withdrawal. These thin membrane tubules nonspecifically bind to the probe and are extruded from the main bilayer with low resistance, often extending tens of microns in length. As each tether either snaps or breaks free of the probe, rapid jumps in tip deflection occur.

Figures 10A, 10B, 10C:
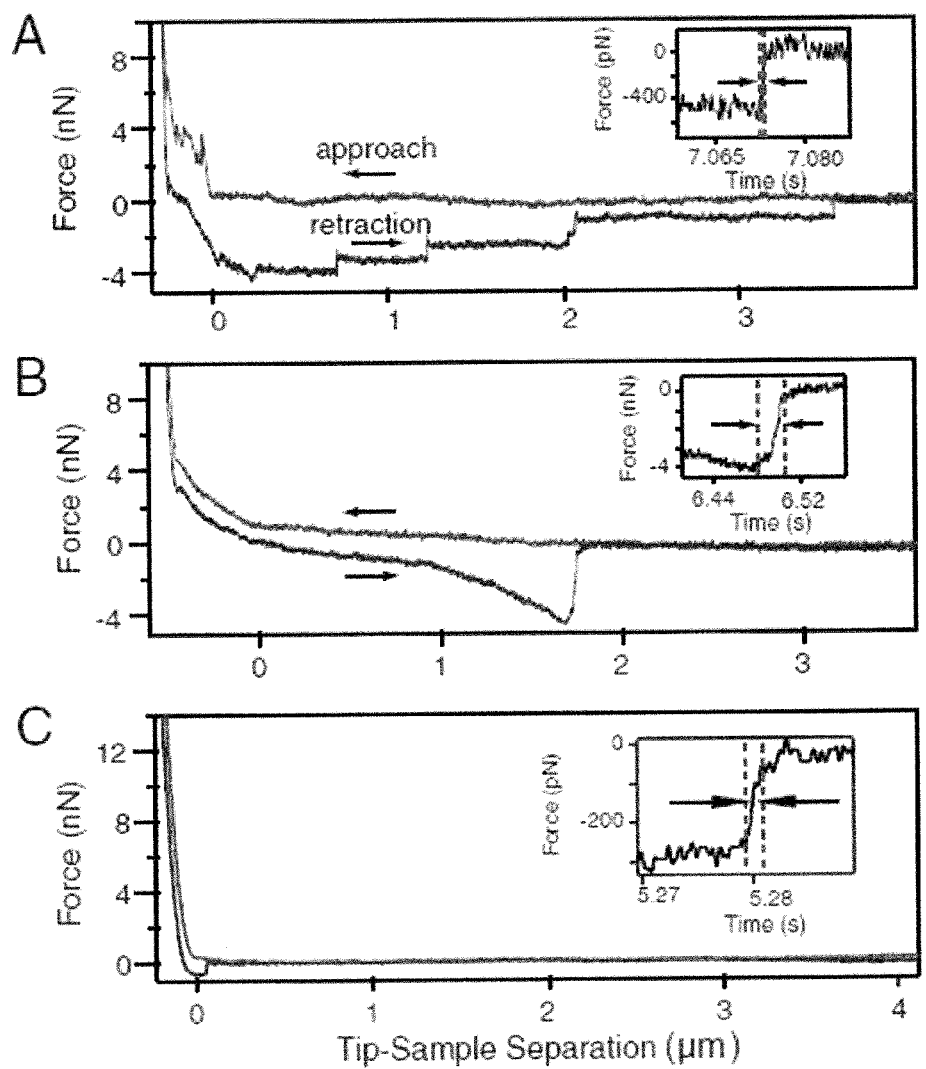
FIGS. 10A-10C show representative AFM force curves for 3 different stealth probes (approach, withdrawal).
Figure 11:
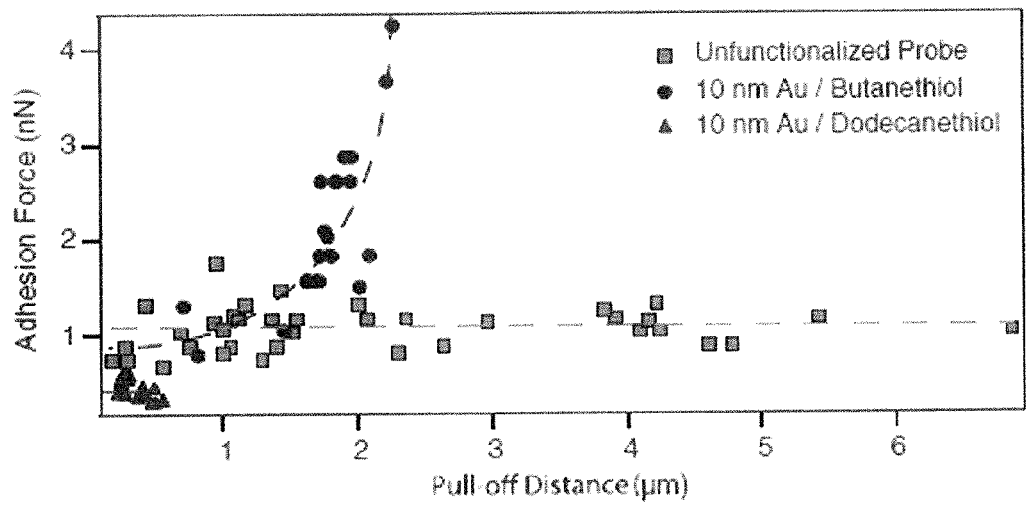
FIG. 11 illustrates adhesion force as a function of pull-off distance. Unfunctionalized probes show behavior consistent with tether formation, namely a constant adhesion force with increasing pull-off distance. Butanethiol functionalized probes exhibit and increase in force with increasing pull-off distance. Dodecanethiol functionalized probes display reduced adhesion compared to both butanthiol and unfunctionalized probes. Dotted lines to guide eye.

The functionalized stealth probes (10 nm Au band) exhibit no penetration force for the first bilayer on approach and only a single pull-off event, signifying spontaneous insertion and formation of a single bilayer-probe interface without membrane tethers (FIGS. 10B and 10C). These failure events occurred over a smaller range of distances than the tethers and with much longer timescales (FIGS. 10A-10C, insets). The duration of the rupture event for the unfunctionalized, butanethiol, and dodecanethiol probes was 0.5±0.26 ms, 7.95±5.5 ms, and 1.87±0.81 ms, respectively. The longer rupture times are consistent with a failure mechanism that involves rearrangement of a number of lipids, as would be expected for the approximately 628 nm lipid-probe contact perimeter (approximately 1800 lipids). The adhesion force as a function of withdrawal distance (FIG. 11) also shows that the butanethiol probe adheres strongly within the bilayer. While unfunctionalized probes have the same rupture force at all distances and large force plateaus consistent with lipid tethers, butanethiol tips have a distinctly nonlinear response that increases with distance. As the probe is withdrawn, the bilayers create a restoring force that increases with distance. An equivalent response has been observed during extraction of membrane proteins that are attached to the underlying cytoskeleton. Similarly, the butanethiol probe must embed firmly enough to cause the subsurface bilayers to mechanically deform before failure. In contrast, the dodecanethiol tips failed almost immediately and no trend in adhesion force could be ascertained. In order to verify that these results were not probe-related artifacts, a dodecanethiol probe was cleaned with UV-ozone, rinsed in ethanol to remove any gold oxide, and then refunctionalized with butanethiol. This yielded nonlinear results equivalent to the other butanethiol probes.

While the locations of the butanethiol and dodecanethiol probes within the bilayer are virtually identical, their adhesion strengths differed considerably, revealing that hydrophobicity alone does not determine the interfacial strength. The average maximum adhesion force for the three different probes shows unfunctionalized probes have an average of 1.05±0.11 nN, butanethiol probes an average of 1.90±0.20 nN, and dodecanethiol probes an average of 0.45±0.08 nN. However, it should be noted that rupture forces and rates are intrinsically linked to the rate at which the bond is loaded. Numerous AFM experiments have shown this dependence, including single-molecule force-clamp experiments and bilayer penetration experiments. Therefore, it may be possible that the observed differences are simply due to differing dependencies on loading rate.

Figures 12A, 12B, 12C:
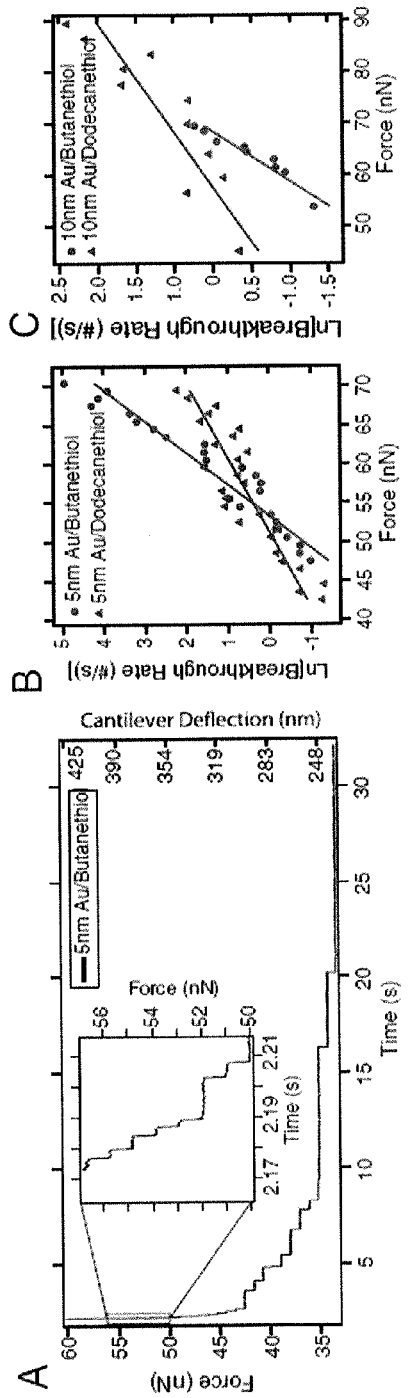
FIG. 12A illustrates force-clamp testing. The force is ramped to a high force load (60 nN) on top of the bilayer stack, then the position of the z-piezo is fixed, and the probe relaxes by breaking though the bilayers. Each stair step corresponds to a single bilayer breakthrough. The breakthrough rate is then measured as a function of the applied force.
FIGS. 12B and 12C show linear fits to ln(k) for the 5 nm (FIG. 12B) and 10 nm (FIG. 12C) band thicknesses for dynamic force spectroscopy reveal butanethiol has a higher adhesion energy than dodecanethiol.

In order to address this question, we measured the energy barrier for bilayer penetration using dynamic force spectroscopy (DFS) experiments. The data was acquired in a force-clamp mode that was performed by rapidly applying a large force load, halting, and allowing the cantilever to relax by breaking through the bilayer stack. FIG. 12A shows a typical force-displacement curve, clearly showing the distinct stair-steps corresponding to bilayer failure. The failure rate (breakthroughs per second) at each force value was then compiled and fit to a standard Langevin model for barrier crossing with applied force:

$$k = A \exp\left(-\frac{E_o - F\gamma}{k_b T}\right)$$

Where k is the failure rate at a given force, A is the attempt frequency (the cantilever resonance frequency of approximately 6 kHz was used), $E_o$ is the unstressed energy barrier height, F is the applied force, T is the absolute temperature, and γ is the location of the energy barrier. FIGS. 12B and 12C show ln(k) vs. F for 5 and 10 nm band thicknesses for both functionalizations and the corresponding linear fits. Both 5- and 10 nm Au bands functionalized with butanethiol exhibit significantly larger energy barriers ($E_{o;5\ nm}$=21.8 $k_b T$, $E_{o;10\ nm}$=15.3 $k_b T$, $\gamma_{5\ nm}$=1.01 pm, $\gamma_{10\ nm}$=0.43 pm), than probes functionalized with dodecanethiol, ($E_{o;5\ nm}$=14.0 $k_b T$, $E_{o;10\ nm}$=10.9 $k_b T$, $\gamma_{5\ nm}$=0.43 pm; $\gamma_{10\ nm}$=0.19 pm), confirming the trend observed during adhesion testing. The adhesion strength for the 5 nm thick bands was higher for either functionalization, likely reflecting the strain required for a single bilayer to conform to a 10 nm band.

Interestingly, the difference between the two functionalized probes agrees with pioneering studies on general anesthetics. Haydon et al. examined the anesthetic properties of n-alkanes infiltrating and swelling lipid bilayers, concluding that homologues shorter than heptane readily adsorb horizontally into the space between leaflets, thereby thickening the bilayer. (see, e.g., Haydon D A, Hendry B M, Levinson S R, "The molecular mechanisms of anesthesia," Nature (1977) 268:356-358; see also Haydon D A, Hendry B M, Levinson S R, Requena J, "Anesthesia by the n-alkanes. A comparative study of nerve impulse blockage and the properties of black lipid bilayer membranes." BBA-Biomembranes (1977) 470: 17-34). Subsequent research using neutron scattering, x-ray diffraction, and differential scanning calorimetry confirmed hexane partitions into the midplane with a horizontal orientation, while longer chain alkanes reside perpendicular to the midplane, parallel to the lipid acyl chains. These results qualitatively agree with the different adhesion forces for the two functionalizations, which are ostensibly oriented in-plane relative to the lipid bilayer and perpendicular to the lipid tails. Butanethiol should prefer the horizontal orientation and indeed has a high adhesion force. Dodecanethiol should favor the vertical orientation, yet it is likely unable to do so from its crystalline structure. The large free energy of the terminal methyl group makes the dodecane-lipid tailgroup intersection quite weak and a likely location to nucleate a defect. Chain mobility may similarly play a role, as butanethiol exists in a disordered, fluid-like phase on planar surfaces compared to the crystalline dodecane, allowing the chain to reorient as necessary.

The implications from the interplay between molecular mobility and hydrophobicity in terms of interface formation extend the possible applications to particle and drug delivery. While surfaces with a mobile, hydrophobic surface functionalization create a strong adhesive bond, restricting mobility decreases the adhesion strength, allowing for short-term association followed by permeation.

These results demonstrate that by recreating the nanometer-scale architecture of transmembrane proteins through a simple microfabrication technique, bioengineered probes can specifically insert into the bilayer core and form a strong interface. The adhesion strength with the bilayer interior may be depended upon the hydrophobicity and molecular mobility of nanoscale hydrophobic bands, allowing tuning with different molecular species. These results indicate the hydrophobic effect may be one factor in material stability within the lipid bilayer, and that mobility and/or chain orientation are other attributes that may be considered in forming the probes described herein. In general, tailoring the bilayer-probe interface characteristics may be possible by altering the probe geometry, including band (e.g., medial heterofunctional region) thickness, number of bands, and molecular functionalization, using the trends demonstrated and illustrated above. Probe penetration dynamics through stacks of lipid bilayers may provide detailed insight into the preferential location of the probe, lipid organization, and adhesion strength. As mentioned, the stealth probe architecture can be fabricated onto atomic force microscope tips or in large arrays on solid substrates.

EXAMPLE 3

In variations of probes (e.g., nanoscale probes) including a medial heterofunctional region, the thickness of the heterofunctional region (which may be a band or annular region) may be selected to enhance the interaction with the membrane into which the probe is to be inserted. In this example we describe the role of nanoscale patterning on the strength of biomembrane-inorganic interfaces. AFM measurements show that inorganic probes functionalized with hydrophobic bands with thicknesses complimentary to the hydrophobic lipid bilayer core exhibit strong attachment in the bilayer. As hydrophobic band thickness increases to 2-3 times the bilayer core the interfacial strength decreases, comparable to homogeneously hydrophobic probes. Analytical calculations and molecular dynamics simulations predict a transition between a 'fused' interface and a 'T-junction' that matches the experimental results, showing lipid disorder and defect formation for thicker bands. These results show that matching biological length scales leads to more intimate bioinorganic junctions, enabling rational design of non-destructive membrane interfaces.

As described above in example 2, mimicking the structure of transmembrane proteins with nanoscale hydrophobic bands (to form the medial heterofunctional region) around post, e.g., a cylindrical atomic force microscope (AFM) tip, may enhance a probe in spontaneously inserting into lipid membranes and forming strong interfaces. By matching the width of the hydrophobic bilayer core with a hydrophobic stripe on an otherwise hydrophilic surface, the lipids would form a seamless interface, even with a sizable diameter probe (FIG. 13A-13G). Electrical measurements confirm that the interface is tight with respect to ion motion, with average resistances over 3 GΩ. Surprisingly, the interfacial strength may not be solely governed by the hydrophobicity of the nanoscale bands, but may also influenced by the identity of the hydrophobic molecules used, with butanethiol and dodecanethiol showing very different behavior.

In this example, we further examine the significance of band thickness relative to bilayer thickness. As the band gets thicker relative to the bilayer core, the lipids must undergo increasing reorganization, which could weaken the interface. A systematic series of band thicknesses is illustrated herein, using AFM interfacial strength measurements with butane and dodecane thiols, combined with molecular dynamics (MD) simulations to reveal the local molecular configurations. We find both the adhesion strength and organization have dependencies on the thickness of the hydrophobic band, highlighting that matching the native biological nanoscale dimensions may help in forming intimately connected bio-inorganic interfaces. Thus, the size of nanostructured hydrophobic bands on membrane penetrating probes can affect the interaction strength and morphology of the inorganic-lipid interface.

Biomimetic stealth probes with Au bands 2, 5, or 10 nm in width were fabricated from commercial silicon AFM cantilevers using a combination of focused ion beam (FIB) milling and metal deposition, as shown in FIGS. 13A-13G. The width was defined from the thickness of an evaporated Au film sandwiched between Cr layers, which could be controlled to be within ±5%. Hydrophobic molecules were self-assembled onto the exposed edge of the Au layer after FIB milling to complete the band. Homogeneously functionalized posts were also fabricated without the band structure for comparison, hereafter referred to as ∞-probes (FIG. 13). Since we had previously found the molecular structure of the hydrophobic functional molecules impacted the interface strength, both butanethiol and dodecanethiol were examined.

Figures 14A, 14B, 14C:
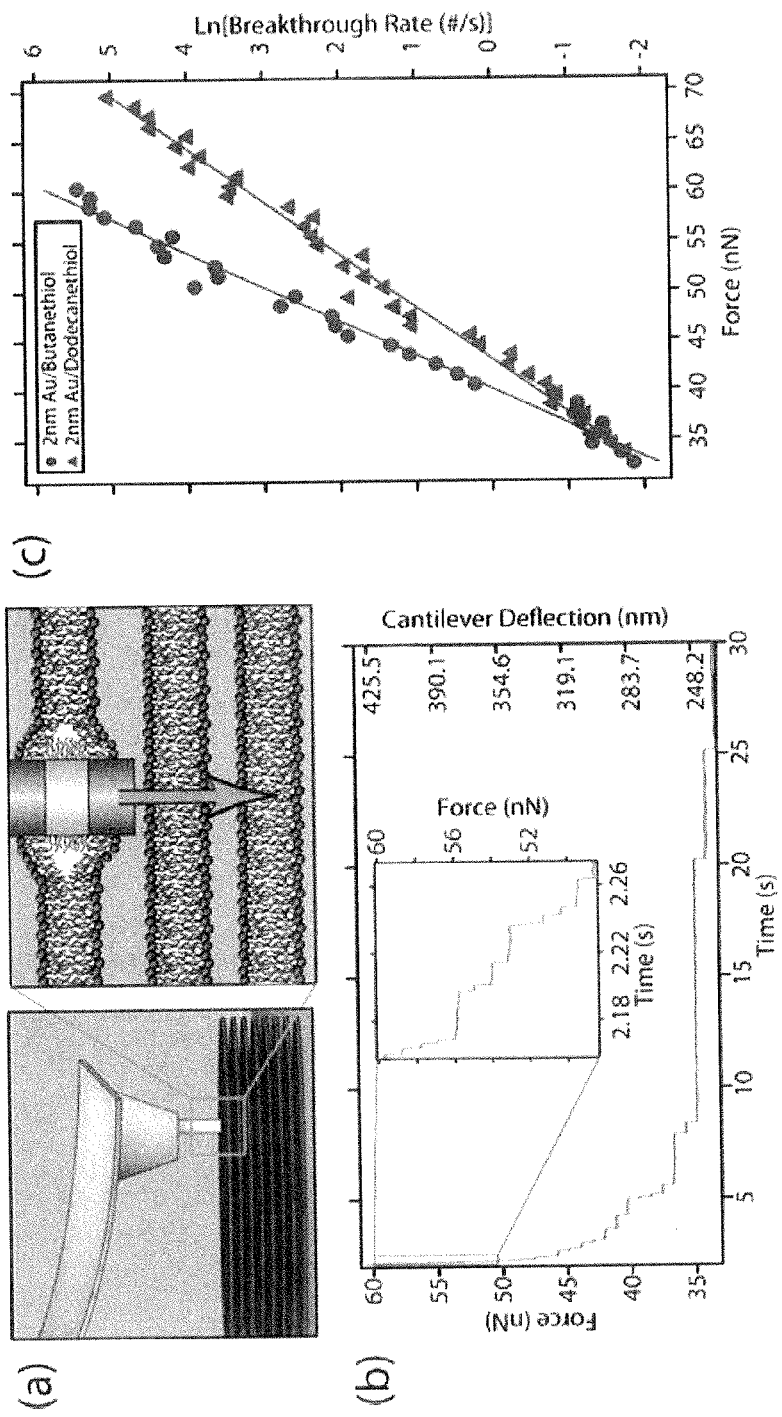
FIGS. 14A-14C show AFM measurements of lipid-probe interface strength.

The interfacial strength of the probe/lipid junction was measured by pushing the functionalized AFM probe tips into a stack of 2:1 SOPC:cholesterol lipid bilayers using a forceclamp approach (FIG. 14A-14C). In this technique, the probes are rapidly loaded to a large force (approximately 60 to 100 nN) against a stack of lipid bilayers by advancing the z-piezo. Following loading, the z-piezo is fixed in position and the cantilever deflection monitored as a function of time as the probes break through each bilayer, penetrating deeper into the stack and reducing the applied load. The resulting displacement or force curves display characteristic stair-steps consisting of rapid jumps when a bilayer fails, followed by uniform plateaus when the tip is loaded on a fresh bilayer (FIG. 14B). By combining several series of curves, the average breakthrough rate (the inverse of the time to failure) as a function of force can be tabulated (FIG. 14C).

The interface strength is then calculated assuming that the probe tear-out and penetration process can be described as crossing an energy-barrier with a set barrier height and position. Many mechanical systems such as protein binding strength and bilayer rupture follow a simple Langevin reaction model under an applied force, which leads to an enhanced reaction rate as a function of load:

$$k = A\exp\left(-\frac{E_0 - F\gamma}{k_b T}\right)$$

where k is the failure rate at a given force, A is the attempt frequency (the cantilever resonance frequency of approximately 6 kHz was used), $E_0$ is the unstressed energy barrier height, F is the applied force, T is the absolute temperature, and g is the location of the energy barrier. By fitting ln(k) as a linear function of force, both $E_0$ and g can be determined (FIG. 14C). The value of the energy barrier reflects both the energy necessary to tear the probe free of the bilayer (the adhesion strength) as well as penetrate the bilayer below it, thus is most properly used to compare strengths between different structures rather than for absolute interfacial energy. This calculation of $E_0$ should also be taken as a lower bound due to the uncertainty of the actual attempt frequency, A, which is likely significantly higher than the cantilever resonance frequency.

Figures 15, 16:
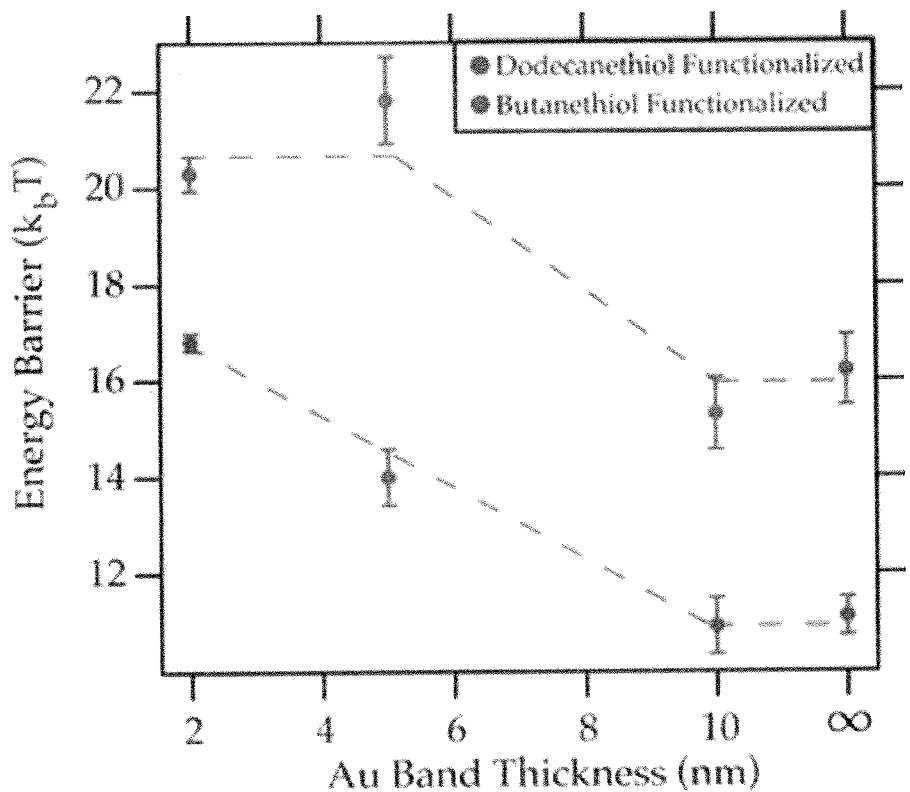
FIG. 15 shows a graph of interfacial strength for a series of different hydrophobic band thicknesses using butanethiol (upper trace) or dodecanethiol (bottom trace) functionalization. Lines added to guide the eye.
FIG. 16 is a table showing calculated bilayer distortion energies ($\Delta G_{def}$) and hydrophobic exposure energies ($\Delta G_{phobic}$) per nm of interface perimeter for each band thickness. Lowest calculated energies are italicized.

The failure energy measurements clearly show that the interfacial strength decreases with increasing band thickness (FIG. 15). For the butanethiol functionalization, the 2 nm band has a high strength of $E_{0,2\ nm}=20.3\pm0.4\ k_b T$, which is maintained for 5 nm thick bands ($E_{0,5\ nm}$=21.8±0.9 $k_bT$). However, the strength dramatically decreases for 10 nm thick bands to $E_{0,10\ nm}$=15.3±0.8 $k_bT$, which is equivalent to the ∞-probes ($E_{0,\infty}$=16.2±0.7 $k_bT$). This emphasizes the importance of matching the inherent nanoscale dimensions, as the 10 nm band, which is just two to three times the thickness of the hydrophobic bilayer core, is functionally equivalent to the infinitely thick case. Dodecanethiol functionalized probes show similar behavior, with 2 nm bands having the highest adhesion energy ($E_{0,2\ nm}$=16.8±0.2 $k_bT$). However, at 5 nm band thicknesses the interface strength has already started to decrease, reaching a value of $E_{0,5\ nm}$=14.0±0.6 $k_bT$ and decaying further to $E_{0,10\ nm}$=10.9±0.6 $k_bT$ at 10 nm thick. Once again the 10 nm case is equivalent to the ∞-probe ($E_{0,\infty}$=11.1±0.4 $k_bT$).

In agreement with our previous results, butanethiol functionalized probes display larger energy barriers than dodecanethiol for all probe geometries. The energy offset between the two functionalizations is very similar for the 2, 10, and ∞-probe cases (3-5 kbT). This suggests that each molecular functionality has a different fundamental interface strength with the bilayer, and the trend observed with band thickness is strictly due to geometry. If the lipid interface to the different molecules changed dramatically we would expect the relative strengths to change as well. The fact that dodecanethiol showed a pronounced strength decrease at 5 nm not present for butanethiol indicates the transition from a stable to weak interface occurs at thinner bands for dodecanethiol. We speculate this may be due to the crystallinity of the dodecanethiol monolayers which may be disrupted at very thin band thicknesses.

The ability of lipid bilayers to accommodate the different band thicknesses can be compared to the bilayer deformations observed for length-mismatched transmembrane proteins. For example, when linear gramicidins, a natural antibiotic peptide from *Bacillus brevis*, dimerize in opposing bilayer leaflets the resulting hydrophobic transmembrane domain length often varies from that of the host bilayer core. When gramicidin is added to synthetic lipid bilayers, X-ray lamellar diffraction experiments detect an increase in the phosphate-to-phosphate distance from 30.8 Angstroms to 32.1 Angstroms for DLPC bilayers, which have a thinner core than the protein, and a decrease from 35.3 to 32.7 Angstroms for DMPC bilayers, which have a thicker core than gramicidin. It has also been shown that a reduction in the bilayer compression and bending moduli can mitigate the decrease in channel lifetimes associated with increasing hydrophobic mismatch. These studies all suggest the bilayer is able to deform to match the hydrophobic protein domain size as opposed to channel distortion or rotation.

The feasibility of the bilayer deforming to create a fused interface for the 2 nm and 5 nm band thicknesses was estimated from the deformation energy based on the theory developed for transmembrane protein-induced distortions. Bilayer deformation energy due to hydrophobic mismatch, $\Delta G_{def}$, was calculated from the bilayer spring constant, $H_B$, the degree of mismatch between the length of the probe's hydrophobic band, $l_p$, and the length of the hydrophobic bilayer core, $l_b$:

$$\Delta G_{def}=H_B(l_p-l_b)^2$$

assuming the intrinsic curvature of an isolated lipid monolayer is negligible. $H_B$ is a function of bilayer area-compression modulus, $K_a$, the bending modulus, $K_c$, $l_b$, and the radius of the bilayer inclusion (in this case, the radius of the stealth probe). Using scaling relations and assuming $K_a$=290 pN $nm^{-1}$ and $l_b$=3.1 nm for 2:1 SOPC:cholesterol bilayers, $H_B$ is found to be 2280 $k_bT\ nm^{-2}$ for a 200 nm diameter probe. The deformation energy for each band thickness is listed in the table shown in FIG. 16. These are compared with the energy necessary to expose the hydrophobic region ($\Delta G_{phobic}$) of either the bilayer core (for $l_p<l_b$) or the functional band (for $l_p>l_b$). With an alkane-water surface energy of approximately 25 mJ $m^{-2}$ and a probe radius of 100 nm, it becomes energetically beneficial to deform the bilayer to match band thicknesses of approximately 1.4<$l_p$<4.8 nm (FIG. 16).

These calculations suggest the fused interface geometry is favorable for 2 nm stealth probes with a slight bilayer compression, similar to transmembrane proteins. The 5 nm band is just outside the calculated stability range (1.5 $k_bT$ higher energy), which would make the interface sensitive to other factors such as molecular structure. Both of these predictions are consistent with adhesion strength experiments. The 2 nm bands had the highest interfacial strength for either functionalization, and while the 5 nm butanethiol probes maintained their strength, dodecanethiol weakened slightly. For 10 nm probes the deformation energy is more than 130 $k_bT$ higher than the hydrophobic surface energy, thus fused interfaces are prohibitory. This is supported by the equivalent behavior of the 10 nm and ∞-probes, showing a fused interface is not formed.

However, these calculations may only apply to the fused interface and do not account for the other possible geometries shown in FIG. 1, which may have lower interfacial energies. While the energy of a 'T-junction' is currently unknown, a rough estimate may be provided by considering the junction to consist of an interstitial void and two rounded hydrophilic one-half caps that form at the band/hydrophilic probe edges. This assumes negligible energy penalty at the alkane/lipid monolayer interface. The void energy is approximately 10 $k_bT\ nm^{-1}$, while the cap energy is derived from the hydrophilic edge energy, about 2.5 $k_bT\ nm^{-1}$. The sum of these components puts the 'T-junction' energy around approximately 13 $k_bT\ nm^{-1}$, which is surprisingly close to the calculated deformation energy values at the experimental transition thickness. Moreover, the energy for a T-junction to a 10 nm band would be equivalent to a 20 nm band or an ∞-probe, since the larger monolayer/alkane interface does not add additional energy, consistent with observations.

The 'ruptured' and 'adhered' junctions are also less likely due to the interface strength's dependence on molecular functionalization for the ∞-probes. The ruptured state has no direct contact with probe, thus the energy barrier for each ∞-probe functionalization should converge to a common value. Instead, there is a consistent approximately 5 $k_bT$ offset. The adhered state is highly energetically unfavorable due to the hydrophilic lipid/hydrophobic probe contact. This could be avoided if another species (such as excess lipid) coated the probe first to make it hydrophilic, yet again there should be no dependence on molecular functionalization in this event. From this set of observations, we conclude that the T-junction is the most likely structure for bands thicker than 5 nm.

The molecular structure of the interface between the nanoscale hydrophobic band and lipid bilayer was further examined through a series of molecular dynamics simulations of planar lipid bilayers coming into contact with hydrophobic bands of different thicknesses. Since this interaction is expected to involve significant rearrangements of lipid bilayer around the hydrophobic band, we chose a coarse-grained lipid model to allow membrane undulations and peristaltic motions (thickness fluctuations). Large scale lipid reorganization such as self-assembly of micelles is known to occur on timescales on the order of 10 ns, while 100 ns are needed to capture the shape fluctuations, necessitating a coarse-grained approach to achieve sufficient integration times. Coarse grained or unified atom models represent small groups of atoms by single interacting 'beads', and have been used extensively to study amphiphilic molecular phase behavior, agglomeration, self-assembly, and large scale shape fluctuations.

Figure 17:
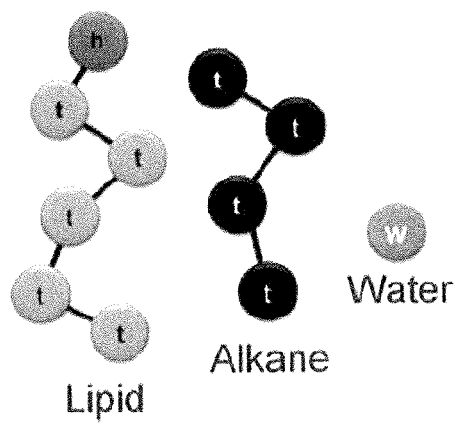
FIG. 17 shows models for various molecules used in the simulation of example 3 (described below), made up of three kinds of particles: h—hydrophilic head, t—hydrophobic tail, w—water.

A lipid model was constructed according to Goetz and Lipowsky, comprised of strings of particles which interact via a Lennard-Jones type interaction potential that is purely repulsive for water-oil interactions but contains short range attraction for like particles. This model was previously used to semiquantitatively describe both molecular scale phenomena such as lipid aggregation or diffusivity in bilayers, and continuum scale phenomena such as membrane elasticity, interfacial tension and membrane bending. In our model, the system is built up from three types of particles (FIG. 17): hydrophilic solvent particles, representing water particles and denoted by 'w'; hydrophilic lipid head group particles denoted by 'h'; and hydrophobic particles for both the alkanes and the tails of the lipids denoted by 't'. The lipids are modeled as a linear chain of one hydrophilic head group particle and five hydrophobic particles for the tail, and the hydrophobic alkane molecules in the band are treated as a linear chain of four hydrophobic particles.

Hydrophobic bands representing the stealth probes were constructed from rows of alkanes tethered on one face of a simulation cell in a straight line. We assume that the curvature of the experimental probe (200 nm diameter) is small relative to the lipid dimensions, and thus approximated as a flat surface. Adjacent alkanes were tethered at a spacing of 4 Angstroms, which is close to the alkanethiol packing observed on the gold surface. To mimic the hydrophilicity of the chromium oxide coated AFM probe, solvent particles were fixed at regular intervals on the remaining area of simulation box face. The hydrophobic ∞-probe was represented by tethering alkanes on the entire face.

Figures 18A, 18B, 18C, 18D, 18E:
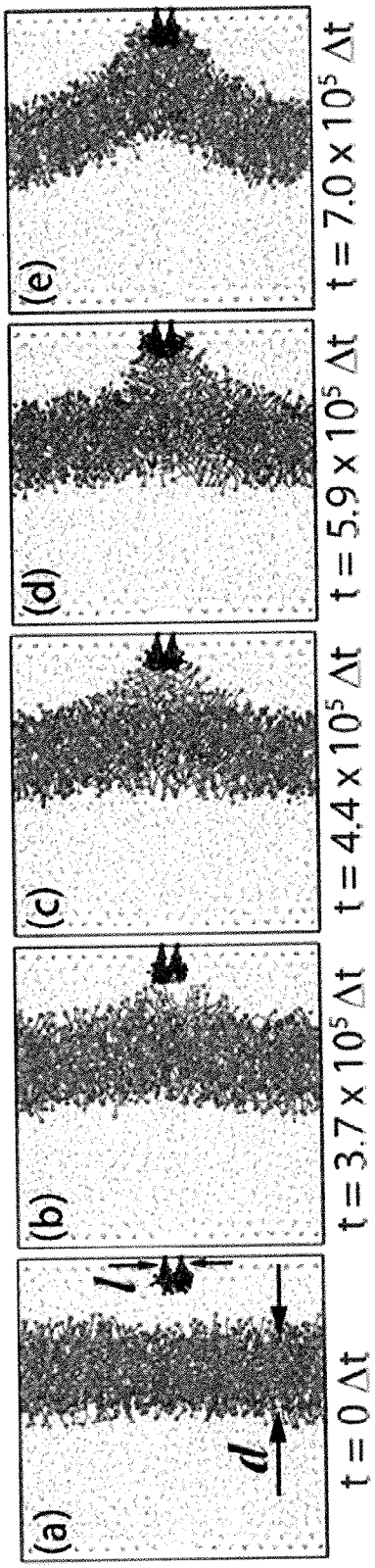
FIGS. 18A-18E illustrate time-resolved fusion of lipid bilayer with hydrophobic band for band thickness, l=(2/5)d. Configurations at various intermediate time points during the simulation are depicted. It took $7 \times 10^5$ time steps for the fusion to complete. Each frame is a projection of a three dimensional simulation box with periodic boundary conditions.

The starting configuration of the system was a continuous, fully relaxed bilayer oriented parallel to an alkane band anchored at one side of a periodic-boundary condition simulation box (FIG. 18A). While this orientation is different than the experimental stack-penetration, it avoids artifacts caused by presupposing a particular edge structure, which would be necessary for any other bilayer configuration. It is also more representative of the case of individual flexible lipid bilayers, such as cell membranes. This arrangement does tend to predispose the overall geometry to adopt a tri-bilayer junction, however, it allows the bilayer to reorganize and expand its area with relative ease, such that the interfacial structure close to the band is still the lowest energy state. The 'fused' and 'T-junction' states (FIG. 1) are thus most properly differentiated by the presence of a void region in the middle of the junction, rather than overall symmetry.

FIG. 18A-18E shows the time-resolved reorganization of the bilayer for a band thickness, l=(2/5)d, where d is the equilibrium thickness of the bilayer (below for additional details). The initial distance between the bilayer mid-plane and the wall face with tethered alkanes was set at 1.5 times the bilayer thickness as shown in FIG. 18A. This separation is chosen such that the range of non-bonded interactions between the alkanes and lipids barely overlap. For the first $3.0 \times 10^5$ time steps, the bilayer shows no visible effect of alkane interaction, and undulates. After approximately $3.0 \times 10^5$ time steps, frequent lipid protrusions from the bilayer leaflet close to the band are observed. At $3.5 \times 10^5$ time steps, coordinated rearrangement of lipids begins as several lipid tails come in contact with the band (FIG. 18C). A well-defined contact region begins to take shape around $4.0 \times 10^5$ time steps as many more lipid tails align with the alkane molecules. The interface at this point is established only at one small region along the length of the band. Subsequently, the fused interface extends along the length of the band, rapidly integrating the entire band with the hydrophobic core of the bilayer. By $6.0 \times 10^5$ time steps, the bilayer leaflet in the vicinity of the band is fused completely; however, the opposite leaflet is still disordered. It takes about $7.0 \times 10^5$ time steps for this leaflet to order and the interface to reach its final structure. This is an ordered 'fused' state, as indicated by the absence of any void regions or hydrophilic head groups trapped in the hydrophobic core, and the band is completely fused with the hydrophobic bilayer core. This structure was stable until the end of the experiment at $1.0 \times 10^6$ time steps.

To study the effect of hydrophobic mismatch in this system and compare to experimental results, the thickness of the hydrophobic band was varied by tethering additional rows of alkanes on the face of the simulation box. FIGS. 19A-19F shows the interface structure between the bilayer and hydrophobic band for different band thickness, while FIGS. 20A-20F show different projections and the 3D simulation box for l=(2/5)d and l=(8/5)d. For band thicknesses l=(2/5)d, (3/5)d, and l=d, a uniform 'fused' interface is observed in all cases with a well-defined hydrophobic core and no interstitial voids. In the top view of FIG. 20A, the interface is clearly homogenous over the entire length of the hydrophobic band. Interestingly, the time to form the interface increases from $6.5 \times 10^5$ time steps for l=(2/5)d to $1.0 \times 10^6$ time steps for l=(3/5)d to $1.5 \times 10^6$ time steps for l=d. Since the number of lipids that participate in the interface and the extent of bilayer rearrangement required scales with the band thickness, this trend is not surprising. Moreover, the structure gradually transitions from being relaxed with a uniform curvature for l=(2/5)d to a tri-bilayer structure for l=d, though at the alkane interface all are 'fused' into the bilayer.

Figures 19A, 19B, 19C, 19D, 19E, 19F:
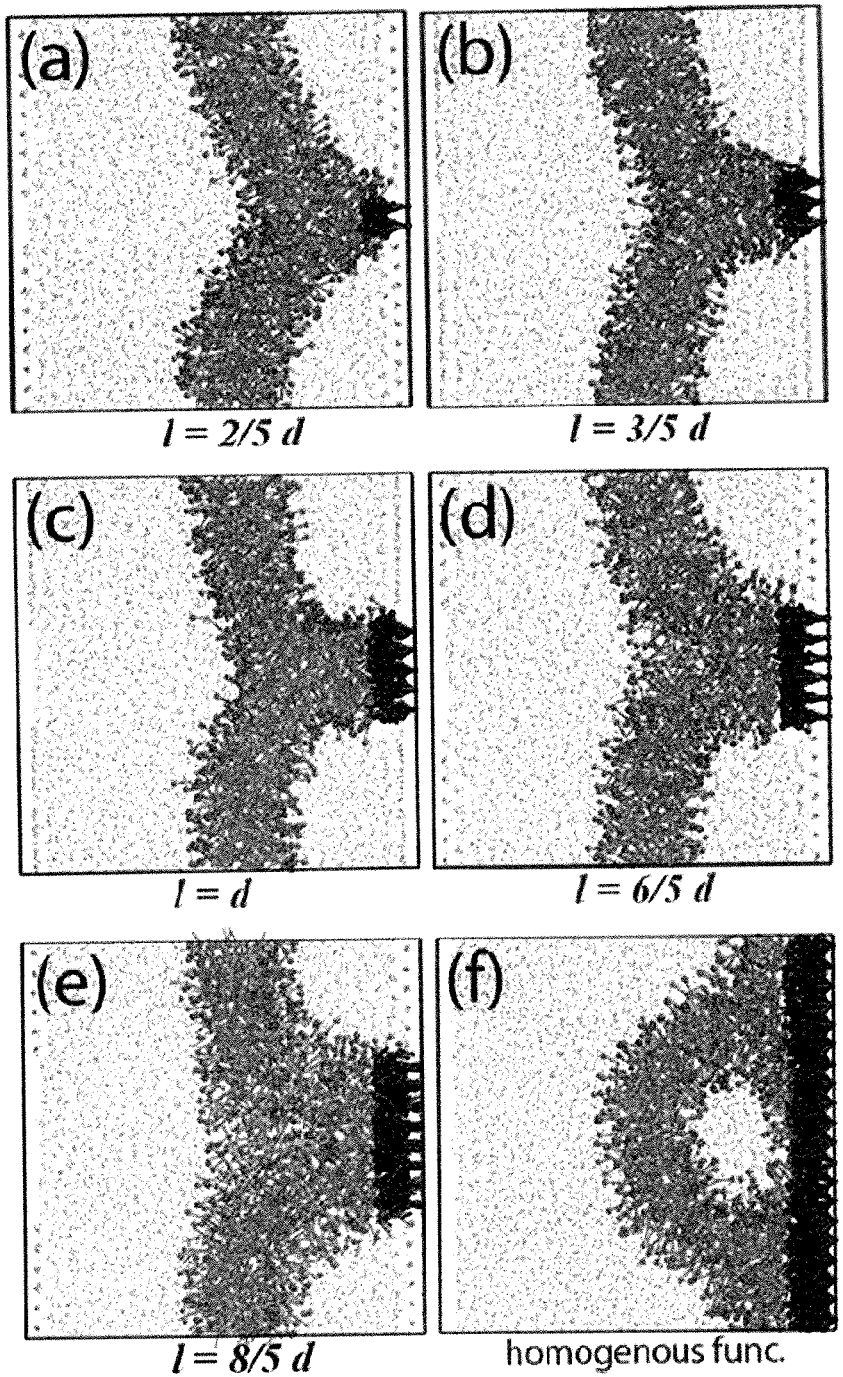
FIGS. 19A-19F illustrate equilibrium interface structures formed after approximately 1 to $1.5 \times 10^6$ time steps for various hydrophobic band thicknesses, where l is band thickness, and d is bilayer thickness.
Figure 20A:
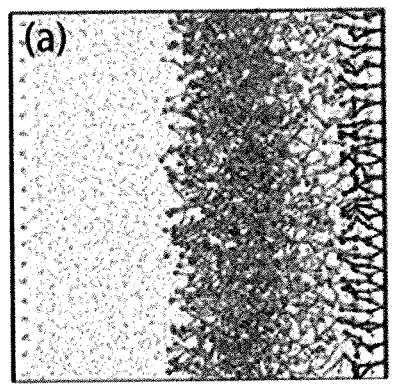
FIGS. 20A-20F illustrate different views of equilibrium interface structures formed after approximately 1 to $1.5 \times 10^6$ time steps for l=(2/5)d and l=(8/5)d.
Figure 20B:
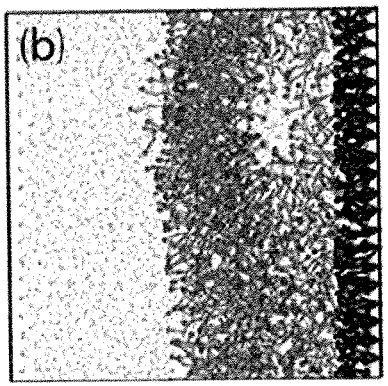
Figure 20C:
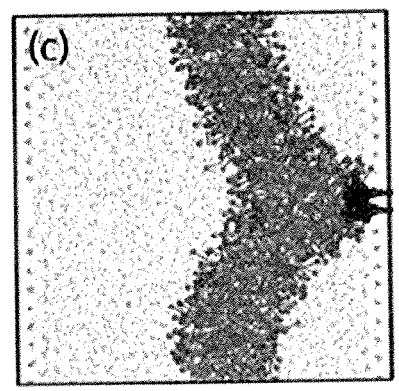
Figure 20D:
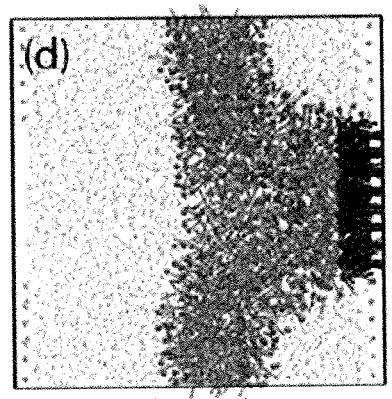
Figure 20E:
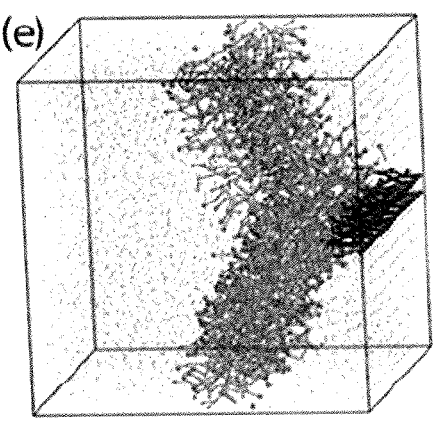
Figure 20F:
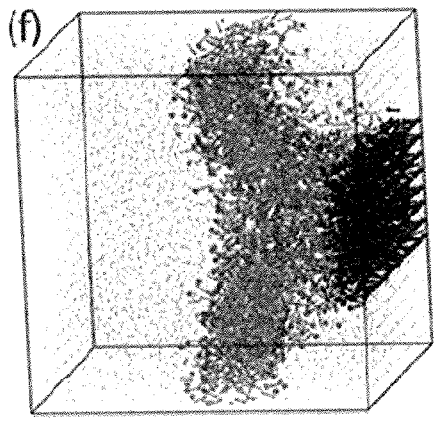

Hydrophobic bands with thicknesses of (6/5)d, (8/5)d, or infinite produced ill-defined structures with disordered interfaces. As the hydrophobic core of the bilayer comes in contact with the hydrophobic band, voids start appearing at the junction. These voids cause the lipids in the vicinity to flip (indicated by the red head groups in the tail region, FIGS. 19D and 19E), disrupting the ordered structure of the bilayer. The structure also varies along the length of the band indicating the formation of a weak interface. At l=(8/5)d, membrane pores form at the interfacial region, as shown in the top view in FIG. 20B. In addition to allowing fluid leakage, pores are known to be nucleation sites for rupture fronts in lipid bilayers, further weakening this uniform along the entire band length (FIGS. 19A-19C). Since this interface lacks defects or other high energy regions like high curvature areas, it is expected to have a high barrier to failure, in line with experimental findings. It should be noted that while both butanethiol and dodecanethiol were used in experiments, the simulations were performed for a generic alkane molecule. Lack of a 3-body term in the alkane model ensures that the alkanes never crystallize, thus the model is more representative of shorter molecules like butanethiol.

Similar to experiments, there is a distinct transition as the band thickness becomes larger than the bilayer thickness. The l=(6/5)d and l=(8/5)d simulations, roughly equivalent to approximately 6 and 8 nm bands, showed dramatically worse organization, as might be expected for the 10 nm thick band result. For such thick band probes, the interface structure appears to be a disordered T-junction with interstitial voids that is heterogeneous along the band length. The T-junction may thus be much less ideal than shown in FIG. 1B, and in fact exist in combination with the fused junction. The coexistence of these two phases is also supported by the partial weakening of the 5 nm dodecanethiol probes, without complete decay to the 10 nm case. For homogenous functionalization that mimics ∞-probes (FIG. 19F), the T-junction structure is much clearer, yet still has defects in the form of voids that cause lipids in the vicinity to disorder. The presence of defects and heterogeneities in the interface structure for these cases could likely result in low interface strengths, in agreement with experimental observations.

Seamlessly integrating inorganic probes into cell membranes is an exciting goal for establishing long-term, nondestructive biointerfaces. In this example we show again that biomimetic probes with nanoscale hydrophobic bands can fuse into the hydrophobic lipid bilayer core. The interfacial strength may be highly sensitive to band thickness, with the strongest interfaces formed for 2 nm thick bands. Both the analytical calculations and MD simulations predicted that as the band thickness exceeded 5 nm the 'fused' interface may no longer be stable, which was also observed experimentally. The agreement between these three different approaches is surprisingly good, indicating that the models developed for transmembrane proteins may also be applied to inorganic devices. The structure of the lipid-probe interface for bands above 5 nm thick is most likely a T-junction state based on analytical energy estimates, MD simulations, and the adhesion strength's dependence on molecular functionality for both the nm and ∞-probes. These junctions may have low interfacial strengths, and simulations show disordered interfaces and a propensity for hole formation. This unstable interface may also help explain why homogenous hydrophobic coatings on patchclamp electrodes do not enhance the electrical seal resistance. On the other hand, thin hydrophobic bands have strong adhesion strengths and well-ordered molecular interfaces, consistent with recent electrical measurements which found very high seal resistances for these probes.

The fact that nm thick bands successfully integrated into lipid membranes shows that matching the nanoscale dimension of biological materials may provide significant benefits for bio-inorganic interfaces, and create an array of new opportunities for drug delivery, electrical measurements and single cell analysis.

Figures 13A, 13B, 13C, 13D, 13E, 13F, 13G:
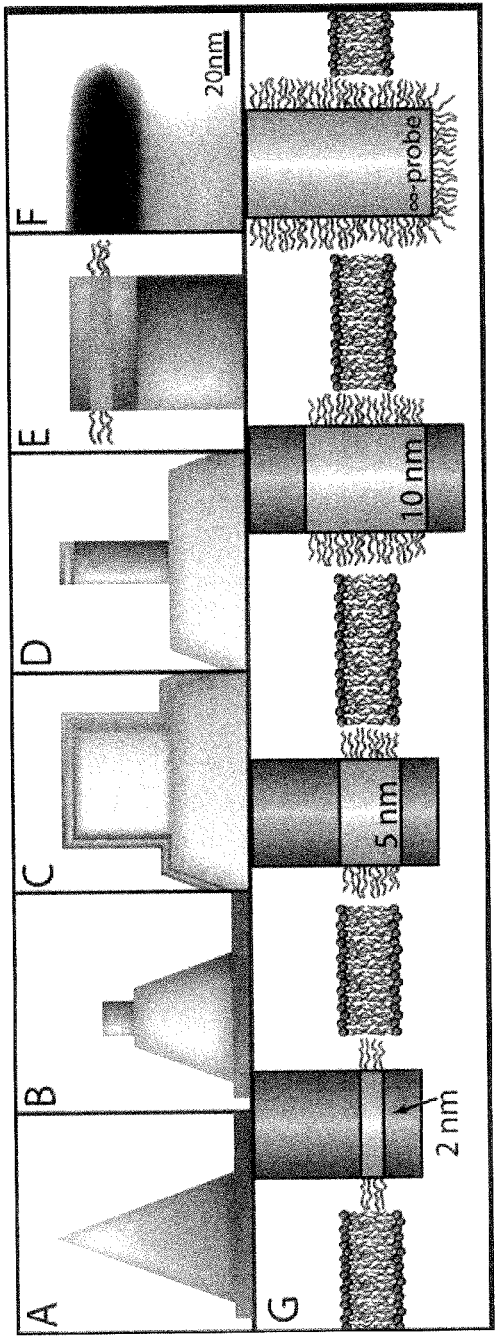
FIGS. 13A-13G illustrate fabrication of hydrophobic bands on AFM cantilever probes.

In example 3, the stealth probes were fabricated as described in example 2. Commercial AFM cantilevers with a nominal spring constant of 0.08 N m$^{-1}$ were mounted vertically in an FIB. The tips were milled to a post shape 500 nm in diameter and 600 nm long using a 30 kV, 10 pA Ga-beam. The tips were then rotated 90° onto their sides and milling repeated to complete the post-geometry (FIG. 13B). A layered Cr—Au—Cr structure (each Cr metal layer=5 nm thick and Au layer=5 or 10 nm) was deposited by e-beam metal evaporation on the modified AFM cantilevers at a rate of 0.5 nm s$^{-1}$ (FIG. 13C) for the 5 nm and 10 nm Au band tips. For 2 nm probes, to deposit the layered Cr—Au—Cr structure (bottom Cr layer=5 nm and Au layer=2 nm; top Cr layer=3 nm), dc magnetron sputtering with 20 mTorr Ar gas in an ultrahigh vacuum chamber of base pressure, approximately 6.2×10$^{-9}$ Torr was utilized. Cr was deposited at a rate of 0.575 Angstrom s$^{-1}$, while Au was deposited at a rate of 0.177 Angstrom s$^{-1}$. ∞-probes were fabricated in a similar manner, except 10 nm Cr was deposited, followed by 20 nm of Au. Thicknesses are ±5% and were calibrated using X-ray reflectivity. Following metal deposition, the cantilevers were remilled in the FIB to a final diameter of approximately 200 nm using the same milling procedure, with the exception of the beam current being reduced to 1 pA (FIG. 13D).

Stacks of 30-2000 lipid bilayers were formed by gentle hydration of a dried lipid cake as described in example 2, above.

Force clamp testing Membrane probes were functionalized for at least 12 h in 5 mM ethanolic solutions of either 1-butanethiol or 1-dodecanethiol. Previously used tips could be re-functionalized with different molecules following a 30 min UV-ozone cleaning. After UV-ozone treatment, tips were soaked in pure ethanol for 30 min to remove any gold oxide.

Functionalized stealth probes were mounted in an Asylum Research MFP-3D AFM. Spring constant calibration was done using the Sader and thermal methods. Stack penetration curves were obtained by initially bringing the probes into contact with a lipid stack at a rate of 4 mm s$^{-1}$. Loading was stopped when a force set point of 60-100 nN was reached. Once the set point was obtained, a 30-60 s dwell was triggered where the z-piezo position was held constant. During this dwell session, the change in cantilever deflection was measured. Drift in the system was accounted for by leveling the low force/long time drift of the baseline.

Force clamp curves were analyzed by measuring the failure rate and force for each bilayer failure. The failure rate was calculated as the inverse of the failure time, measured from the first point after a breakthrough event to the first point of the following breakthrough. The failure force was the average force during this interval (FIG. 14). The individual failure events were binned in force, and breakthrough rate plotted as a function of force. Energy barriers were then determined by fitting.

In the analysis above, non-bonded interactions between one hydrophilic and one hydrophobic particle were treated with a truncated repulsive soft core potential of the following form:

$$U_9(r) = 4\varepsilon_0 \left(\frac{r}{\sigma_{SC}}\right)^{-9} - 4\varepsilon_0 \left(\frac{r_c}{\sigma_{SC}}\right)^{-9} + \frac{36\varepsilon_0}{r_c}\left(\frac{r_c}{\sigma_{SC}}\right)^{-9}(r - r_c)$$

Other non-bonded interactions were calculated with a truncated Lennard-Jones potential:

$$U_{6-12}(r) = 4\varepsilon_0\left(\left(\frac{r}{\sigma}\right)^{-12} - \left(\frac{r}{\sigma}\right)^{-6}\right) + Br + A$$

$$B = \frac{4\varepsilon_0}{r_c}\left(12\left(\frac{r_c}{\sigma}\right)^{-12} - 6\left(\frac{r_c}{\sigma}\right)^{-6}\right), A$$

$$= -4\varepsilon_0\left(\left(\frac{r_c}{\sigma}\right)^{-12} - \left(\frac{r_c}{\sigma}\right)^{-6}\right) - Br_c$$

These potentials are truncated such that $U_{9\ or\ 6-12}=0$ and $dU_{9\ or\ 6-12}/dr=0$ at $r=r_c$. A uniform cut-off radius of $r_c=2.5\sigma$ is assumed for all non-bonded interactions. The parameter $\sigma_{SC}$ is chosen to be $\sigma_{SC}=1.05\sigma$. For the bonded potential, a harmonic spring force with equilibrium distance s and spring constant $k=5000\varepsilon/\sigma^2$ is chosen so that up to 10% of the bonds of a given configuration differ by more than 2% from the long time average bond length equal to σ. The bonded potential is given by:

$$U_{bond}(r) = k(r-\sigma)^2$$

The fundamental scales of length (σ), mass (m) and energy (ε) are chosen such that $N_{AV}m=36$ g mol$^{-1}$, $\sigma=0.33$ nm, and $N_{AV}\varepsilon=2$ kJ mol$^{-1}$, where $N_{AV}=6.022\times10^{23}$ mol$^{-1}$. This implies that each hydrophobic tail particle 't' corresponds to about 2-3 CH$_2$ groups. Thus, the lipid with 5 tails corresponds to about 13 CH$_2$ groups, while a four particle long alkane chain is roughly equivalent to dodecane. The temperature is kept constant during the simulation at 324 K which is equivalent to an energy scale of $N_{AV}\epsilon=2$ kJ mol$^{-1}$. The time scale for the model can be calculated from $\sigma$, m and $\epsilon$ as $\sigma^2=$m $\sigma^2/\epsilon$. For the parameters chosen here, this time scale, $\sigma$ is approximately 1.4 ps. The time step for the simulation was chosen as 1 fs which is close to $\tau/2000$ used previously.

Molecular dynamics simulations were performed under the NVT ensemble. The size of the box was chosen to be 80 Angstroms×80 Angstroms×80 Angstroms. The choice of the number of lipids in the system was based on the previous study of the effect of lipid concentration on membrane tension in a fixed volume system. It has been shown that a non-dimensional average head group area of about 2.4 for freely jointed chain lipids similar to the ones used in this study produces bilayers with negligible tension. Any higher or lower lipid densities cause either positive or negative membrane tension, while still assembling into stable bilayers. Using the length scale of $\sigma=3.33$ Angstroms, for a total projected area of 80×80 Angstroms, an average head group area of approximately 2.4 corresponds to about 500 lipids. To keep the volume density of the particles in the box same as previous work, the total number of particles was kept constant at approximately 9500.

Lipid bilayers, stable for $2\times10^6$ time steps, are preassembled using a combination of conjugate gradient energy relaxation and molecular dynamics simulation starting from an initially random configuration of molecules. On these timescales, membrane undulations and lipid protrusions can be observed. The equilibrated bilayer is observed to have an average non-dimensional thickness, d of 6, measured as the average separation between parallel planes running through the lipid head groups in each leaflet. All simulations were performed using the MD++ software package at constant temperature, volume and number of particles. To keep the temperature constant, a Nose-Hoover thermostat was applied. The atomic equations of motion were integrated using the Velocity-Verlet algorithm. The time step was fixed at $\Delta t=1$ fs. With this time step, the fluctuation of the Hamiltonian over $1\times10^6$ time steps is on the order of $10^2$ eV. Since the total energy of the system is on the order of $10^9$ eV, this fluctuation is about 7 orders of magnitude smaller, indicating that the choice of time step is adequate. Periodic boundary conditions were applied in all three directions to eliminate any edge effects. Visualization was performed using Atomeye.

EXAMPLE 4

Although many of the examples and figures described herein discuss the nanoscale probes that include a medial heterofunctional region (typically a hydrophobic band between two hydrophilic or less hydrophobic regions), in some variations the probes described herein do not include this region. The nanoscale (which may also be referred to as nanoposts or nanowires) having this hydrophobic region represent a subset of probes fabricated to the dimensions and specifications illustrated above.

For example, returning now to FIG. 2A, a nanoscale device may be configured as a post extending from a base region to an overall height of less than about 10 nm, 7 nm, 5 nm, 2 nm, 1 nm, 0.5 nm, etc. The diameter of the post may be less than 2 µm, and in some variations is less than 1 µm, or less than 0.5 µm. For example, the diameter may be less than 200 nm. As discussed above, the post may have a cylindrical, conical, pyramidal, tubular, or any other appropriate structures. In some variations, the post extends proud from the base.

In general, the posts include at least two separate regions, a distal region and a proximal region. The proximal region is typically insulated and non-reactive, while the distal region is typically reactive. For example, the distal region may be functionalized (as discussed above, the distal region may include one or more markers, binding partners, or the like for engaging one or more cellular components, and/or for releasing one or more molecules (including drugs) and/or for indicating a marker of cellular status or activity (e.g., ion concentration or flux, protein concentration, nucleotide binding, etc.). In some variations the distal region is an electrochemically active region that may be used to sense and/or apply electrical potential, as discussed above in the context of FIGS. 2A-2E. In some variations the posts may include multiple distal regions (e.g., both a distal electrochemically active region and a functionalized region); the two regions may overlap. For example, a functionalized region may be formed on top of an electrochemically active region.

In some variations, the probes described herein do not necessarily penetrate the cell membrane, but may be engulfed by the cell membrane (at least partially) and may form a seal thereto. For example, in some variations the cell may sit on top of the probe projecting from the base. In some variations the probes do not penetrate the cell membrane, but the nanoscale probe still pokes into the cell membrane, forming an invagination cavity in the cell membrane in which the probe resides.

Further, in some variations a plurality of probes may be configured adjacent each other on a substrate (e.g., a chip-based platform). A single cell may be penetrated by the probe, or each probe may be targeted to a single cell. As mentioned briefly above, in some variations multiple probes (a pair, group, or cluster of probes and/or posts) may be spaced less than the average cell diameter may for instance all interact with the same cell. This may allow additional capabilities such as using one electrode as a current injector, and another as a voltage detector, thereby reducing or eliminating contact resistance issues. Alternatively, the multiple posts could be used to measure the activity in different regions of the cells with less resistance, or to triangulate the origin of electrical activity.

In use, one or more of the nanoscale probes described herein may be included as part of another system or device for use with biological cells and/or tissue. As discussed above, the nanoscale probes described herein may be used as part of a screening procedure and system, in which cells are placed in contact with the probes and the probes may be used to 'read out' information from the cells. Because the probes described herein provide intimate access to the cell (e.g., cell membrane and cytoplasm, as well as potentially other internal cell structures), these probes may offer a powerful means for monitoring and manipulating cells, and therefore entire tissues and organs. Because the probes described herein are capable of achieving long-lasting and stable connection with cells, the probes may also be incorporated as part of an implant (e.g., an electrode) for patient monitoring and/or treatment.

Although various illustrative embodiments are described above, any of a number of changes may be made to various embodiments without departing from the scope of the invention as described by the claims. For example, the multiple regions and components of the probes described herein (e.g., functionalized regions, heterofunctional regions, electrochemically active regions, insulator regions, etc.) may be combined in any combination or arrangement, unless expressly indicated otherwise. Further, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Specifically, the examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of electrically recording from a cell, the method comprising:
   contacting a cell membrane with a probe electrode comprising a base region and a post projecting from the base region, the post having a diameter of less than about 2 µm, a distal electrochemically active region, a proximal non-electrochemically active region, and a medial heterofunctional region between the distal electrochemically active region and the proximal non-electrochemically active region, wherein the medial heterofunctional region is more hydrophobic than either the distal electrochemically active region or the proximal non-electrochemically active region;
   forming a seal with the cell membrane so that the electrochemically active region is in electrical communication with the cell and the medial heterofunctional region is held in the cell membrane; and
   recording electrical activity with the probe electrode.

2. A method of establishing stable intracellular transmembrane access with a cell, the method comprising:
   contacting the cell with a probe electrode having a base region and a post projecting from the base region, the post having a distal electrochemically active region and a proximal non-electrochemically active region, wherein the distal electrochemically active region is separated from the proximal non-electrochemically active region by a medial heterofunctional region forming a hydrophobic band around the post; and
   fusing the hydrophobic band into the cell membrane.

3. A probe electrode for inserting through a cell membrane, the probe electrode comprising:
   a base region including an electrical contact; and
   a post projecting distally from the base region, the post having a diameter of less than about 2 µm, the post comprising:
      a distal electrochemically active region in electrical communication with the electrical contact;
      a proximal non-electrochemically active region that is electrically insulating and adjacent to the base region;
      a medial heterofunctional region between the distal electrochemically active region and the proximal non-electrochemically active region, the medial heterofunctional region configured to form an annular hydrophobic region between the distal electrochemically active region and the proximal non-electrochemically active region.

4. A probe electrode for sealing with a cell membrane, the probe electrode comprising:
   a base region including an electrical contact; and
   a post projecting from the base region, the post having a diameter of less than about 2 µm, the post comprising:
      a distal electrochemically active region in electrical communication with the electrical contact;
      a proximal non-electrochemically active region adjacent to the base region; and
      a medial heterofunctional region between the distal electrochemically active region and the proximal non-electrochemically active region, wherein the medial heterofunctional region is more hydrophobic than either the distal electrochemically active region or the proximal non-electrochemically active region.

5. The probe electrode of claim 4, wherein the post comprises a diameter of less than 1000 nm.

6. The probe electrode of claim 4, wherein the distal electrochemical region has a height of between about 20 nm and about 5 µm.

7. The probe electrode of claim 4, wherein the distal electrochemical region is nanoporous.

8. The probe electrode of claim 4, wherein the distal electrochemical region comprises one or more of: Pt; PtO; Ir; IrO; $Ir_2O_3$; $IrO_2$; Ru; $RuO_2$; diamond; Au; graphite; Ni; V; Co; W; Mn; oxides of: Pt, PtO, Ir, IrO, $Ir_2O_3$, $IrO_2$, Ru, $RuO_2$, diamond, Au, graphite, Ni, V, Co, W, Mn; polyanaline; and poly(3,4 ethylene dioxythiophene).

9. The probe electrode of claim 4, further comprising a conductive region in electrical contact with the distal electrochemically active region that extends through the proximal non-electrochemically active region to a connector on the base.

10. The probe electrode of claim 4, wherein the non-electrochemically active region of the probe is formed of the same material as the base.

11. The probe electrode of claim 4, wherein the proximal non-electrochemically active region comprises an electrically insulative material.

12. The probe electrode of claim 4, wherein the post comprises a conical shape.

13. The probe of claim 4 wherein the medial heterofunctional region has a width of less than 200 nm.

14. The probe of claim 4 wherein the medial heterofunctional region has a width of between about 5 and about 10 nm.

15. The probe of claim 4, further comprising a secondary medial region distal to the medial heterofunctional region configured to form a hydrophobic region.

16. The probe electrode of claim 4, wherein the medial heterofunctional region forms a hydrophobic ring between the distal electrochemically active region and the proximal non-electrochemically active region.

17. The probe electrode of claim 4, further comprising a distal functionalized region distal to the proximal non-electrochemically active region, wherein the distal functionalized region comprises an activity marker configured to indicate a cellular state or activity.

18. A probe electrode for inserting though a cell membrane, the probe electrode comprising:
- a base region;
- a post projecting from the base region, the post having a diameter of less than about 2 µm, the post comprising:
  - a distal electrochemically active region;
  - a proximal non-electrochemically active region adjacent to the base region comprising an electrically insulating material; and
  - a medial heterofunctional region between the distal electrochemically active region and the proximal non-electrochemically active region, wherein the medial heterofunctional region is configured to form a region that is more hydrophobic than either the distal electrochemically active region or the proximal non-electrochemically active region.

19. The probe electrode of claim 18, wherein the distal electrochemical region has a height of between about 20 nm and about 5 µm.

20. The probe electrode of claim 18, wherein the distal electrochemical region is nanoporous.

21. The probe electrode of claim 18, further comprising a conducive region in electrical contact with the distal electrochemically active region that extends through the proximal non-electrochemically active region to a connector on the base region.

22. The probe electrode of claim 18, wherein the non-electrochemically active region of the probe is formed of the same material as the base region.

23. The probe electrode of claim 18, further comprising an electrical contact on the base region.

24. The probe electrode of claim 18, wherein the medial heterofunctional region comprises an annular ring configured to bind to a molecule to form an annular hydrophobic region separating the distal electrochemically active region and the proximal non-electrochemically active region.

25. The probe of claim 18 wherein the medial heterofunctional region has a width of less than 200 nm.

26. The probe of claim 18 wherein the medial heterofunctional region has a width of between about 5 and about 10 nm.

27. The probe electrode of claim 18, further comprising a distal functionalized region distal to the proximal non-electrochemically active region, wherein the distal functionalized region comprises an activity marker configured to indicate a cellular state or activity.

28. The probe electrode of claim 18, further comprising a secondary medial region distal to the medial heterofunctional region configured to form a hydrophobic region.

* * * * *